(12) United States Patent
Suzuki et al.

(10) Patent No.: US 10,881,143 B2
(45) Date of Patent: Jan. 5, 2021

(54) NON-BURNING TYPE FLAVOR INHALER, FLAVOR SOURCE UNIT, AND ATOMIZING UNIT

(71) Applicant: JAPAN TOBACCO INC., Tokyo (JP)

(72) Inventors: Akihiko Suzuki, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 380 days.

(21) Appl. No.: 15/798,640

(22) Filed: Oct. 31, 2017

(65) Prior Publication Data
US 2018/0049477 A1  Feb. 22, 2018

Related U.S. Application Data

(63) Continuation of application No. PCT/JP2016/062854, filed on Apr. 22, 2016.

(30) Foreign Application Priority Data

May 1, 2015  (WO) .................. PCT/JP2015/063099

(51) Int. Cl.
| | |
|---|---|
| *A24F 47/00* | (2020.01) |
| *A61M 15/06* | (2006.01) |
| *A61M 11/04* | (2006.01) |
| *A24F 40/30* | (2020.01) |
| *H05B 3/46* | (2006.01) |

(52) U.S. Cl.
CPC ............ *A24F 47/008* (2013.01); *A24F 40/30* (2020.01); *A24F 47/00* (2013.01); *A61M 11/042* (2014.02); *A61M 15/06* (2013.01); *H05B 3/46* (2013.01)

(58) Field of Classification Search
CPC ............................ A24F 47/004; A24F 47/008
See application file for complete search history.

(56) References Cited

U.S. PATENT DOCUMENTS

| | | | | |
|---|---|---|---|---|
| 4,677,995 | A | * | 7/1987 | Kallianos ............... A24D 3/041 131/335 |
| 2007/0062548 | A1 | | 3/2007 | Horstmann et al. |
| 2008/0092912 | A1 | | 4/2008 | Robinson et al. |

(Continued)

FOREIGN PATENT DOCUMENTS

| | | |
|---|---|---|
| CN | 203897285 U | 10/2014 |
| CN | 203952438 U | 11/2014 |

(Continued)

OTHER PUBLICATIONS

International Search Report, issued in PCT/JP2016/062854 (PCT/ISA/210), dated Aug. 2, 2016.

(Continued)

*Primary Examiner* — Eric Yaary
(74) *Attorney, Agent, or Firm* — Birch, Stewart, Kolasch & Birch, LLP

(57) ABSTRACT

A flavor inhaler includes: an aerosol flow path for guiding, to the mouthpiece side, an aerosol generated by an atomizing part; and an acid flow path for guiding, to the mouthpiece side, an acid discharged from an acid generating source without allowing the acid to pass through the atomizing part. The aerosol flow path includes at least a first flow path for guiding the aerosol to the mouthpiece side through a flavor inhalation component source.

16 Claims, 12 Drawing Sheets

(56) References Cited

U.S. PATENT DOCUMENTS

| | | | |
|---|---|---|---|
| 2010/0242976 A1 | 9/2010 | Katayama et al. | |
| 2013/0192620 A1* | 8/2013 | Tucker | A24F 47/004 131/329 |
| 2013/0340778 A1 | 12/2013 | Liu | |
| 2014/0060556 A1* | 3/2014 | Liu | A24F 47/008 131/329 |
| 2014/0261488 A1 | 9/2014 | Tucker | |
| 2015/0313282 A1* | 11/2015 | Ademe | A24F 47/008 131/329 |
| 2016/0205998 A1 | 7/2016 | Matsumoto et al. | |
| 2016/0235121 A1* | 8/2016 | Rogan | A24D 3/041 |

FOREIGN PATENT DOCUMENTS

| | | |
|---|---|---|
| CN | 204273248 U | 4/2015 |
| EP | 2989912 A1 | 3/2016 |
| GB | 2524856 A | 10/2015 |
| JP | 2007-512880 A | 5/2007 |
| JP | 2010-506594 A | 3/2010 |
| JP | 2010-104310 A | 5/2010 |
| JP | 5041555 B2 | 10/2012 |
| JP | 2014-528718 A | 10/2014 |
| WO | WO 2013/116558 A1 | 8/2013 |
| WO | WO 2014/110119 A1 | 7/2014 |
| WO | WO 2015/046386 A1 | 4/2015 |
| WO | WO 2015/197627 A1 | 12/2015 |

OTHER PUBLICATIONS

Chinese Office Action and Search Report, dated Aug. 2, 2019, for Chinese Application No. 201680025382.0, with an English translation.

Japanese Office Action dated Mar. 1, 2019, for corresponding Japanese Patent Application No. 2017-516590, with machine translation.

Korean Office Action, dated Oct. 26, 2018, for Korean Application No. 10-2017-7031148, with an English translation.

Extended European Search Report, dated Dec. 17, 2018, for European Application No. 16789513.5.

Canadian Office Action, dated Sep. 18, 2018, for corresponding Canadian Application 2,984,454.

Japanese Office Action, dated Aug. 7, 2018, for corresponding Japanese Application No. 2017-516590, with an English machine translation.

* cited by examiner

US 10,881,143 B2

NON-BURNING TYPE FLAVOR INHALER, FLAVOR SOURCE UNIT, AND ATOMIZING UNIT

CROSS REFERENCE TO RELATED APPLICATIONS

This application is a Continuation of PCT International Application No. PCT/JP2016/062854, filed on Apr. 22, 2016, which claims priority under 35 U.S.C. 119(a) to Patent Application No. PCT/JP2015/063099, filed in Japan on May 1, 2015, all of which are hereby expressly incorporated by reference into the present application.

TECHNICAL FIELD

The present invention relates to: a non-burning type flavor inhaler having an atomizing unit having an atomizer configured to atomize an aerosol source without burning; and a flavor source unit and an atomizing unit configured to be connectable to the non-burning type flavor inhaler.

BACKGROUND ART

Conventionally, a non-burning type flavor inhaler for inhaling flavor without burning is known. The non-burning type flavor inhaler has: an atomizing unit configured to atomize an aerosol source without burning; and a tobacco source provided on a mouthpiece side compared to the atomizing unit (for example, refer to Patent Literatures 1 and 2).

CITATION LIST

Patent Literature

Patent Literature 1: Japanese Unexamined Patent Application Publication No. 2010-506594
Patent Literature 2: Japanese Granted Patent No. 5041555

SUMMARY OF THE INVENTION

A first feature is summarized as a non-burning type flavor inhaler comprising: an atomizing unit having an atomizer configured to atomize an aerosol source without burning, a flavor source provided on a mouthpiece side compared to the atomizing unit, an acid source configured to release an acid, an aerosol flow path configured to guide an aerosol generated from the atomizing unit to the mouthpiece side, and an acid flow path configured to guide the acid released from the acid source to the mouthpiece side without passing through the atomizer, wherein the aerosol flow path includes at least a first flow path configured to guide the aerosol to the mouthpiece side while passing through the flavor source.

A second feature according to the first feature is summarized as that the acid flow path is a flow path configured to guide an acid to the mouthpiece side without passing through the flavor source.

A third feature according to the first feature or the second feature is summarized as that the flavor source is provided between the acid source and the atomizing unit, in a flow path communicating with the acid source and the atomizing unit at a downstream of the acid source.

A fourth feature according to the third feature is summarized as that the flavor source is provided between the acid source and the atomizing unit, in all of the flow path communicating the acid source and the atomizing unit at the downstream of the acid source.

A fifth feature according to any one of the first feature to the fourth feature is summarized as that the flavor source is a tobacco source.

A sixth feature according to the fifth feature is summarized as that the flavor source is a tobacco source, and the tobacco source has alkaline pH in water solution obtained by adding water of which weight ratio is 10 times to the tobacco source.

A seventh feature according to the first feature is summarized as that the acid flow path is a flow path configured to guide an acid to the mouthpiece side while passing through the flavor source.

An eighth feature according to any one of the first feature to the seventh feature is summarized as that the aerosol flow path, in addition to the first flow path, includes a second flow path which is different from the first flow path.

A ninth feature according to the eighth feature is summarized as that a reduction rate of an aerosol in the second flow path is smaller than a reduction rate of an aerosol in the first flow path.

A tenth feature according to the eighth feature or the ninth is summarized as that the acid flow path is common to at least a part of the second flow path.

An eleventh feature according to any one of the tenth feature to the seventh feature is summarized as that the acid source is provided in the second flow path.

A twelfth feature according to any one of the eighth feature to the eleventh feature is summarized as that at least a part of the first flow path is a flow path of the aerosol generated from the atomizer, and at least a part of the second flow path is a flow path of the aerosol generated from another atomizer which is different from the atomizer.

A thirteenth feature according to any one of the first feature to the tenth feature is summarized as that the atomizer does not exist at an upstream of the acid source.

A fourteenth feature according to any one of the first feature to the thirteenth feature is summarized as the non-burning type flavor inhaler comprising: a first ventilation hole for introducing air to the atomizing unit; and a second ventilation hole provided separately from the first ventilation hole and configured to introduce an air to the acid source.

A fifteenth feature according to the fourteenth feature is summarized as the non-burning type flavor inhaler comprising: a flavor source unit having the flavor source and a unit main body configured to house the flavor source, wherein the unit main body is configured to connectable to an inhalator main body constituting the non-burning type flavor inhaler, the inhalator main body has the second ventilation hole, the unit main body has an airflow path in which the acid source is provided, and at least one of the inhalator main unit and the unit main body has a positioning function for specifying a relative position between the inhalator main body and the unit main body so that the second ventilation hole communicates with the airflow path.

A sixteenth feature according to any one of the first feature to the fifteenth feature is summarized as the non-burning type flavor inhaler comprising: a mixing chamber for mixing a flavor component captured by the aerosol generated from the atomizing unit and the acid released from the acid source.

A seventeenth feature is summarized as a flavor unit comprising:
 a flavor source; and a unit main body configured to be connectable to an inhalator main body constituting a non-burning type flavor inhaler and housing the flavor source, wherein in a state where the unit main body has been connected to the inhalator main body, at least a part of an aerosol flow path configured to guide to a mouthpiece side, an aerosol generated from an atomizing unit configured to atomize an aerosol source without burning is formed, and at least a part of an acid flow path configured to guide an acid released from an acid source to the mouthpiece side without passing through the atomizing unit is formed, and the aerosol flow path provided in the flavor source unit includes at least a first flow path configured to guide the aerosol to the mouthpiece side while passing through the flavor source.

An eighteenth feature according to the seventeenth feature is summarized as that the flavor source is a tobacco source.

A nineteenth feature according to the eighteenth feature is summarized as that the flavor source is a tobacco source, and the tobacco source has alkaline pH in a water solution obtained by adding water of which weight ratio is 10 times to the tobacco source.

A twentieth feature according to any one of the seventeenth feature to the nineteenth feature is summarized as that the acid flow path provided in the flavor source unit is a flow path configured to guide an acid to the mouthpiece side without passing through the flavor source.

A twenty first feature according to any one of the seventeenth feature to the twentieth feature is summarized as that the aerosol flow path provided in the flavor source unit, in addition to the first flow path, includes a second flow path which is different from the first flow path.

A twenty second feature according to the twenty first feature is summarized as that a reduction rate of an aerosol in the second flow path is smaller than a reduction rate of an aerosol in the first flow path.

A twenty third feature according to the twenty first feature or the twenty second feature is summarized as that the acid flow path provided in the flavor source unit is common to at least a part of the second flow path.

A twenty fourth feature according to the twenty third feature is summarized as that the acid source is provided in the second flow path.

A twenty fifth feature according to any one of the twenty first feature to the twenty fourth feature is summarized as that at least a part of the first flow path is a flow path of an aerosol generated from the atomizer, and at least a part of the second flow path is a flow path of an aerosol generated from another atomizer which is different from the atomizer.

A twenty sixth feature according to any one of the twenty first feature to the twenty third feature is summarized as that in a state where the unit main body has been connected to the inhalator main body, the atomizer does not exist at an upstream of the acid source.

A twenty seventh feature according to any one of the seventeenth feature to the twenty sixth feature is summarized as the flavor source unit comprising: a mixing chamber for mixing the aerosol generated from the atomizing unit and the acid released from the acid source is provided.

A twenty eighth feature is summarized as an atomizing unit comprising: an atomizer configured to atomize an aerosol source which does not include a nicotine component, without burning; an acid source configured to release an acid; and a connector configured to connect a flavor source at a downstream of the atomizer so that an aerosol generated from the atomizer is guided to the flavor source, wherein the acid released from the acid source is guided to a mouthpiece side without passing through the atomizer.

MODE FOR CARRYING OUT THE INVENTION

Figure 1:
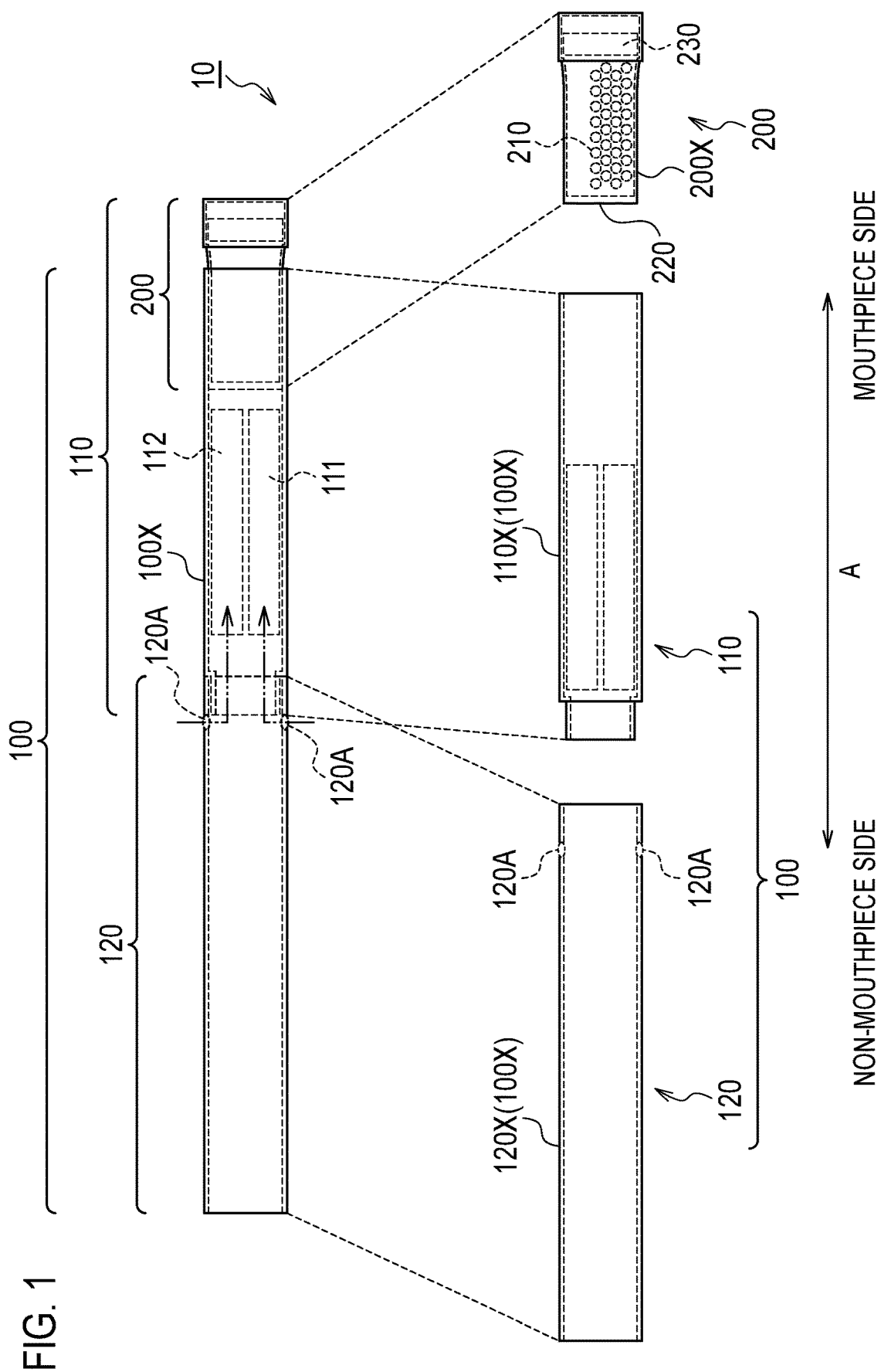
FIG. 1 is a view showing a non-burning type flavor inhaler 10 according to a first embodiment.

Hereinafter, embodiments of the present invention will be described. In the following description of the drawings, the same or similar reference numerals denote the same or similar parts. It should be noted that the drawings are schematic, and the ratios of dimensions and the like may be different from the actual ones.

Therefore, specific dimensions and the like may be determined by referring to the following description. Of course, the drawings may include the parts having different dimensions and ratios.

OVERVIEW OF THE EMBODIMENT

Under the background technique described above, as a result of utmost study, the Inventor, et al. found out that a flavor can be improved by adding an acid to an aerosol configured to capture a flavor component by passing through a tobacco source. On the other hand, as in Patent Literature 2 described above, if an acid is easily added to an aerosol source, a member (for example, electric heat wire) constituting an atomizing unit is degraded by the acid.

A non-burning type flavor inhaler according to an embodiment comprises: an atomizing unit having an atomizer configured to atomize an aerosol source without burning, a flavor source provided on a mouthpiece side compared to the atomizing unit, an acid source configured to release an acid, an aerosol flow path configured to guide an aerosol generated from the atomizing unit to the mouthpiece side, and an acid flow path configured to guide the acid released from the acid source to the mouthpiece side without passing through the atomizer. The aerosol flow path includes at least a first flow path configured to guide the aerosol to the mouthpiece side while passing through the flavor source.

First Embodiment (Non-Burning Type Flavor Inhaler)

Hereinafter, a non-burning type flavor inhaler according to a first embodiment will be described. FIG. 1 is a view showing a non-burning type flavor inhaler 10 according to the first embodiment. The non-burning type flavor inhaler 10 is a device for inhaling a flavor component without burning, and has a shape extending along a predetermined direction A which is a direction from a non-mouthpiece end to a mouthpiece end. Incidentally, hereinafter, it is to be noted that the non-burning type flavor inhaler 10 is simply referred to as a flavor inhalator 10.

As shown in FIG. 1, the flavor inhalator 10 has an inhalator main body 100 and a cartridge 200.

The inhalator main body 100 constitutes a main body of the flavor inhalator 10, and has a shape capable of connecting the cartridge 200. The inhalator main body 100 has a first unit 110 and a second unit 120. Specifically, the inhalator main body 100 has a cylinder 100X, and the cartridge 200 is connected to a mouthpiece end of the cylinder 100X.

The first unit 110 has a first cylinder 110X constituting a part of the cylinder 100X. The first unit 110 has: an atomizing unit 111 configured to atomize an aerosol source without burning; and an acid source 112 configured to release an acid. The atomizing unit 111 and the acid source 112 are housed in the first cylinder 110X.

In the first embodiment, the atomizing unit 111 has a reservoir 111P, a wick 111Q, and an atomizer 111R. The reservoir 111P holds the aerosol source. For example, the reservoir 111P is a porous body composed of a material such as a resin web. The wick 111Q inhales the aerosol source held by the reservoir 111P. For example, the wick 111Q is composed of a glass fiber. The atomizer 111R atomizes the aerosol source inhaled by the wick 111Q. The atomizer 111R is composed of an electric heat wire wound around the wick 111E in predetermined pitches.

The aerosol source is a liquid such as polyalcohol. The polyalcohol is glycerin, propylene glycol, 1.3-propane diol, sorbitol, or a combination thereof. The aerosol source may not include a nicotine component. The aerosol source, for example, as described above, is held by the porous body composed of the material such as the resin web. The porous body may be composed of a non-cigarette material or may be composed of a cigarette material.

Incidentally, the aerosol source may include a flavor source containing a flavor component. Alternatively, the aerosol source may not include the flavor source containing the flavor component. It is preferable that the aerosol source that does not include the flavor source have substantially neutral pH. The substantial neutral pH is pH of 7±1. In this manner, there can be attained an advantageous effect of improvement of a flavor with a mixture of an acid, which will be described later, while restraining damage to the atomizer 111R exerted by the acid released from the acid source 112 or an alkali component included in the flavor source 210.

The first embodiment exemplifies, as an atomizing unit 111, a heating type unit configured to atomize the aerosol source by way of heating. However, the atomizing unit 111 may be an ultrasonic wave type unit configured to atomize the aerosol source by way of ultrasonic wave.

The acid source 112 releases an acid. As the acid, there can be employed: an inorganic acid (such as a phosphoric acid); a saturated fatty acid; an unsaturated fatty acid; a saturated fatty cyclic acid; an unsaturated fatty cyclic acid; an aromatic acid (including a heterocyclic polycyclic aromatic); or an organic acid (such as a polycarboxylic acid, a hydroxy acid, an alkoxy acid, a keto acid, and a hydrofluoric acid, a thiosulfate acid, an amino acid) or a combination thereof. For example, the acid includes: for example, a 3-methyl-2-hydroflouric valeric acid; a pyruvic acid; a 2-hydrofluoric valeric acid; a 4-methyl-2-hydrofluoric valeric acid; a 3-methyl-2-hydrofluoric butanoic acid; a 2-hydrofluoric octanic acid; a 4-hydrofluoric valeric acid; a 2,3,4,5-tetrahydroxy adipic acid (galactaric acid); a 2,3-dihydroxy benzoic acid; a 2,5-dihydroxy benzoic acid (gentisic acid); a 3,5-dihydroxy benzoic acid; a 4-acetoamido benzoic acid or a combination thereof.

In the first embodiment, the acid released from the acid source 112 is volatized by the air flow generated by inhalation, and has a steam pressure at which the acid can be delivered up to the mouthpiece side. Although it is preferable that the acid source 112 include, for example, a volatile acid (such as an acid having a steam pressure of 0.1 kPa or more at 20° C., for example), the embodiment is not limitative thereto. The acid source 112 may include a nonvolatile acid or a hardly volatile acid (for example, an acid having a steam pressure which is less than 0.1 kPa at 20° C.) and heating means and the acid may be volatized by heating. Incidentally, in a case in which a nonvolatile acid or a hardly volatile acid is employed at a normal temperature, if an aerosol passes through the acid source 112, the acid source 112 may not include the heating means (for example, the aspects shown in FIG. 13, FIG. 15, and FIG. 16). A flavor such as menthol may be imparted to the acid source 112.

In the first embodiment, it is to be noted that the acid source 112 is disposed in line with the atomizing unit 111 in the vertical direction relative to the predetermined direction A.

Figure 2:
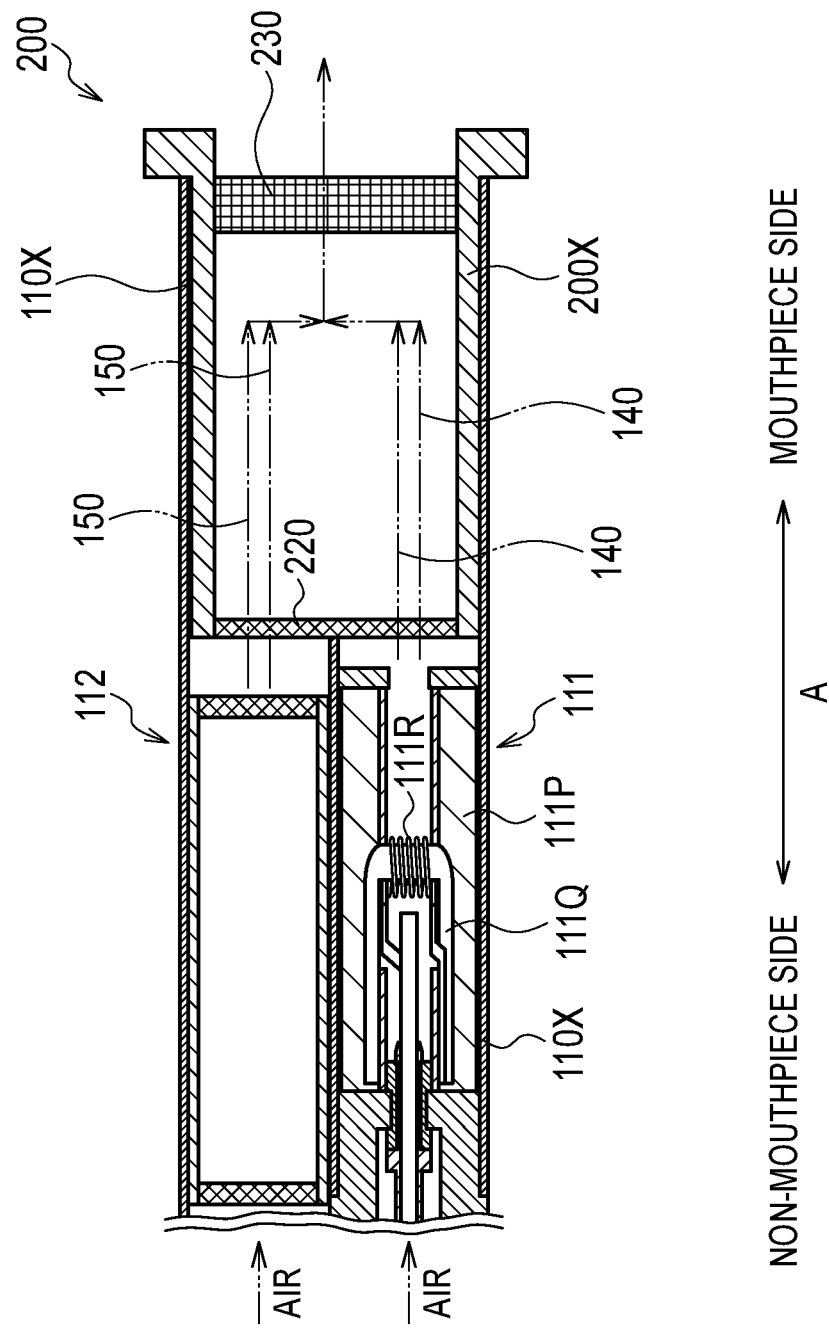
FIG. 2 is a view for illustrating an aerosol flow path according to the first embodiment.

The second unit 120 has a second cylinder 120X constituting a part of the cylinder 100X. The second unit 120 is an electrical unit having: a power source configured to drive the flavor inhalator 10; and a control circuit configured to control the flavor inhalator 10. The power source and the control circuit are housed in the second cylinder 120X. The power source is a lithium ion battery, for example. The control circuit is composed of a CPU and a memory, for example. In the first embodiment, the second unit 120 has a ventilation hole 120A. The air introduced from the ventilation hole 120A, as shown in FIG. 2, is introduced to the atomizing unit 111 (atomizer 111R) and the acid source 112.

The cartridge 200 is an example of the flavor source unit configured to be connectable to the inhalator main body 100 constituting the flavor inhalator 10. The cartridge 200 is provided on the mouthpiece side compared to the atomizing unit 111 in the flow path of the gas (hereinafter, referred to as "air") inhaled from the mouthpiece. In other words, the cartridge 200 does not always need to be provided on the mouthpiece side compared to the atomizing unit 111 in terms of a physical space, and may be provided on the mouthpiece side compared to the atomizing unit 111 in the aerosol flow path configured to guide the aerosol generated from the atomizing unit 111 to the mouthpiece side. That is, in the first embodiment, it may be considered that the "mouthpiece side" is a synonym for "upstream" in the flow of an aerosol.

Specifically, the cartridge 200 has a cartridge main body 200X, a flavor source 210, a mesh 220, and a filter 230.

The cartridge main body 200X has a cylindrical shape extending along the predetermined direction A. The cartridge main body 200X houses the flavor source 210.

The flavor source 210 is provided on the mouthpiece side compared to the atomizing unit 111 in the flow path of the air inhaled from the mouthpiece. The flavor source 210 imparts the flavor component to the aerosol generated from the aerosol source. In other words, the flavor imparted to the aerosol by the flavor source 210 is transported to the mouthpiece.

In the first embodiment, the flavor source 210 is composed of a raw material piece configured to impart the flavor component to the aerosol generated from the atomizing unit 111. The flavor component includes the nicotine component or the like, for example. It is preferable that the size of the raw material piece be 0.3 mm or more and 1.2 mm or less. Further, it is preferable that the size of the raw material piece be 0.2 mm or more and 0.7 mm or less. The smaller the size of the raw material piece constituting the flavor source 210 is, the larger specific surface area is, and thus, the flavor component is easily released from the raw material piece constituting the flavor source 210. Therefore, the amount of the raw material piece can be restrained when a desired amount of the flavor component is imparted to the aerosol. As the raw material piece constituting the flavor source 210, tobacco, a molded member obtained by molding the cigarette raw material in a granular manner can be employed. However, the flavor source 210 may be a molded member obtained by the cigarette raw material in a sheet shape. In addition, the raw material piece constituting the flavor source 210 may include the flavor component, and does not always need to be composed of the cigarette raw material. A flavor such as menthol may be imparted to the flavor source 210.

Here, the raw material piece constituting the flavor source 210 is obtained by screening in conformance with JIS Z 0015 by using the stainless screen in conformance with JIS Z 8801. For example, by using the stainless screen having an aperture of 0.71 mm, for example, the raw material piece is screened over 20 minutes by a dry-type and machine-type screening technique to thereby obtain the raw material piece passing through the stainless screen having the aperture of 0.71 mm. Subsequently, by using a stainless screen having an aperture of 0.212 mm, the raw material piece is screened over 20 minutes by the dry-type and machine-type screening technique to thereby remove the raw material piece passing through the stainless screen having the aperture of 0.212 mm. That is, the raw material piece constituting the flavor source 210 is a raw material piece which passes through the stainless screen configured to define an upper limit (aperture=0.71 mm) and does not pass through the stainless screen configured to specify a lower limit (aperture=0.212 mm). Therefore, in the embodiment, the lower limit of the size of the raw material piece constituting the flavor source 210 is defined by the aperture of the stainless screen configured to specify the low limit. Incidentally, the upper limit of the size of the raw material piece constituting the flavor source 210 is defined by the aperture of the stainless screen configured to specify the upper limit.

In the first embodiment, the flavor source 210 is a tobacco source to which a basic substance has been added (for example, an example of flavor source including nicotine component). It is preferable that pH of the water solution obtained by adding water of which weight ratio is 10 times to the tobacco source be greater than 7, and it is more preferable that the pH be 8 or more. Thus, the flavor component generated from the tobacco source can be efficiently removed by the aerosol. Therefore, the amount of the tobacco source can be restrained when a desired amount of the flavor component is imparted to the aerosol. On the other hand, it is preferable that pH of the water solution obtained by adding water of which weight ratio is 10 times to the tobacco source be 14 or less, and it is more preferable that the pH be 10 or less. In this manner, the damage to the flavor inhalator 10 (for example, cartridge 200 or inhalator main body 100) can be restrained.

Incidentally, it is to be noted that the flavor and smoking generated from the flavor source 210 is carried by the aerosol, and there is no need to heat the flavor source 210 per se.

The mesh 220 is provided so as to close the aperture of the cartridge main body 200X on the non-mouthpiece side relative to the flavor source 210, and the filter 230 is provided so as to close the aperture of the cartridge main body 200X on the mouthpiece side relative to the flavor source 210. The mesh 220 has coarseness to an extent such that the raw material piece constituting the flavor source 210 does not pass. The coarseness of the mesh 220 has an aperture of 0.077 mm or more and 0.198 mm or less, for example. The filter 230 is composed of a substance having ventilation property. It is preferable that the filter 230 be an acetate filter, for example. The filter 230 has coarseness to an extent such that the raw material piece constituting the flavor source 210 does not pass.

(Aerosol Flow Path and Acid Flow Path)

Hereinafter, an aerosol flow path and an acid flow path according to the first embodiment will be described. FIG. 2 is a view for illustrating the aerosol flow path and the acid flow path according to the first embodiment. Specifically, FIG. 2 is a sectional schematic view showing an internal structure of the flavor inhalator 10 in a state where the cartridge 200 has been connected to the inhalator main body 100.

As shown in FIG. 2, the flavor inhalator 10 has an aerosol flow path 140 and an acid flow path 150.

The aerosol flow path 140 is a flow path configured to guide the aerosol generated from the atomizing unit 111 to the mouthpiece side. In other words, in the state in which the cartridge 200 has been connected to the inhalator main body 100, the aerosol flow path 140 configured to guide the aerosol generated from the atomizing unit 111 to the mouthpiece side is formed.

In the first embodiment, the aerosol flow path 140 is composed of a first flow path configured to guide the aerosol to the mouthpiece side while passing through the flavor source 210.

The acid flow path 150 is a flow path configured to guide the acid released from the acid source 112 to the mouthpiece side without passing through the atomizing unit 111 (atomizer 111R). In other words, in the state in which the cartridge 200 has been connected to the inhalator main body 100, the acid flow path 150 configured to guide the acid generated from the acid source 112 to the mouthpiece side is formed. In the example shown in FIG. 2, the acid flow path 150 is a flow path configured to guide the acid to the mouthpiece side while passing through the flavor source 210.

In the first embodiment, the flavor component captured by the aerosol generated from the atomizing unit 111 and the acid released from the acid source 112 are mixed with each other in the cartridge 200. In other words, the aerosol flow path 140 and the acid flow path 150 have a common flow path in the cartridge 200.

In the first embodiment, the flavor source 210 is provided between the acid source 112 and the atomizing unit 111, in the flow path communicating with the acid source 112 and the atomizing unit 111 at the downstream of the acid source 112. In more detail, it is preferable that the flavor source 210 be provided between the acid source 112 and the atomizing unit 111, in all of the flow path communicating with the acid source 112 and the atomizing unit 111 at the downstream of the acid source 112. Here, it is to be noted that the flow path communicating with the acid source 112 and the atomizing unit 111 is a flow path in which not only the gas guided from the upstream to the downstream passes, but also the gas guided from the downstream to the upstream can pass.

Incidentally, the "flow path" means a space in which the gas guided from the upstream to the downstream passes in inhaling operation, and it may be considered that the "flow path" means a physical space connecting two locations to each other. In addition, in a case where the term "pass" or "not pass" is used as a definition of the "flow path", it is to be noted that the paraphrase that "the gas generated or released from a portion A passes through a portion B" means that the gas guided from the upstream to the downstream passes through the portion B, and means that the portion B is provided at the downstream of the portion A. On the other hand, it is to be noted that the paraphrase that "the gas generated or released from a portion A does not pass through a portion B" means that the gas guided from the upstream to the downstream does not pass through the portion B, and means that the portion B does not provided at the downstream of the portion A. For example, the paraphrase "the acid flow path configured to guide the acid released from the acid source to the mouthpiece side without passing through the atomizer" means that the atomizer does not exist on the downstream side of the acid source, and means that the atomizer is disposed on the upstream side of the acid source or is disposed in parallel to the acid source.

That is, it is to be noted that, in the example shown in FIG. 2, after the cartridge 200 has been connected to the inhalator main body 100, even if an airflow from the downstream to the upstream arises, the acid released from the acid source 112 is hardly directly guided to the atomizing unit 111. In addition, it is to be noted that, even if the acid released from the acid source 112 has diffused, the acid released from the acid source 112 is hardly directly guided to the atomizing unit 111.

In the first embodiment, in the state in which the cartridge main body 200X has been connected to the inhalator main body 100, at least a part of the aerosol flow path 140 configured to guide the aerosol generated from the atomizing unit 111 configured to atomize the aerosol source without burning is formed, and at least a part of the acid flow path 150 configured to guide the acid generated from the acid source 112 to the mouthpiece side without passing through the atomizer 111R is formed. In other words, at least a part of the aerosol flow path 140 and at least a part of the acid flow path 150 are formed of the cartridge main body 200X.

Here, it is to be noted that the members constituting the acid flow path 150 (such as cylinder 100X, cartridge main body 200X, and mesh 220, for example) are composed of a member having acid resistivity.

(Functions and Advantageous Effects)

In the first embodiment, the acid flow path 150 configured to guide the acid to the mouthpiece side without passing through the atomizer 111R is provided and thus the flavor can be improved while degradation of the members constituting the atomizing unit 111 is restrained.

In the first embodiment, in the flow path communicating with the acid source 112 and the atomizing unit 111 (in all of the flow path), the flavor source 210 is provided between the acid source 112 and the atomizing unit 111. Therefore, the acid generated from the acid source 112 is hardly directly guided to the atomizing unit 111, and degradation of the members constituting the atomizing unit 111 hardly arises. Further, the flavor source 210 is a tobacco source (having alkaline pH in water solution obtained by adding water of which weight ratio is 10 times to the tobacco source) and thus the acid released from the acid source 112 is neutralized by the flavor source 210; and therefore, the acid generated from the acid source 112 is hardly directly guided to the atomizing unit 111, and degradation of the members constituting the atomizing unit 111 hardly arises.

In the first embodiment, the flavor source 210 is a tobacco source (having alkaline pH in a water solution obtained by adding water of which weight ratio is 10 times to the tobacco source). Therefore, the flavor generated from the tobacco source can be efficiently removed by the aerosol, and a loss of the consumption quantity of the aerosol source can be reduced. The flavor component can be efficiently removed and thus the amount of the tobacco source can be restrained when the desired amount of the flavor component is obtained.

In the first embodiment, the atomizing unit 111 (atomizer 111R) does not exist at the upstream of the acid source 112. In other words, the aerosol flow path 140 is a flow path configured to guide the aerosol generated by the atomizing unit 111 (atomizer 111R) to the mouthpiece side without passing through the acid source 112. Therefore, the aerosol is not filtrated by the acid source 112, and the flavor can be improved while a loss of the aerosol is restrained.

Modification Example 1

Figure 3:
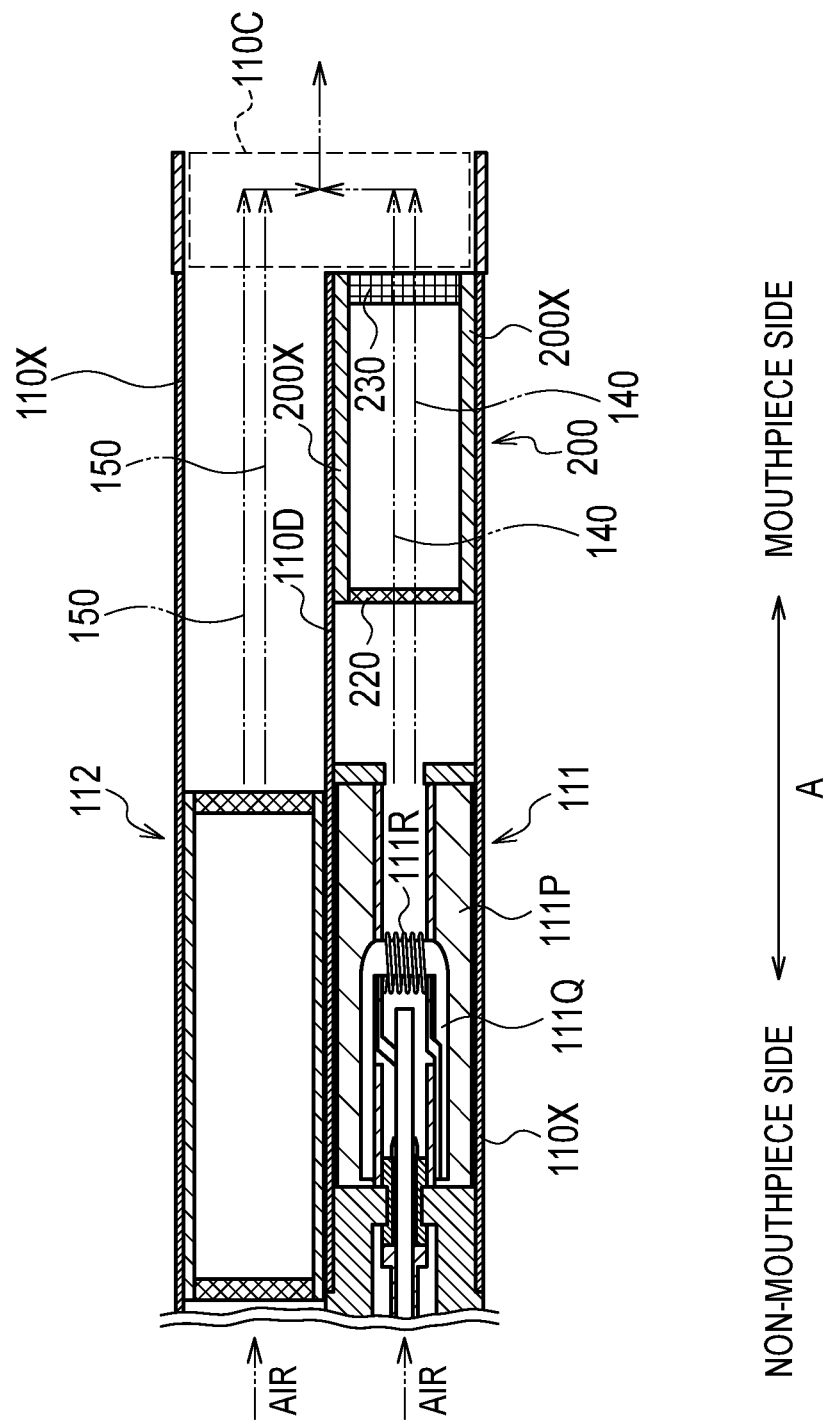
FIG. 3 is a view for illustrating an aerosol flow path 140 and an acid flow path 150 according to Modification Example 1.

Hereinafter, Modification Example 1 of the first embodiment will be described with reference to FIG. 3. FIG. 3 is a sectional schematic view showing an internal structure of a flavor inhalator 10 in a state where a cartridge 200 has been connected to an inhalator main body 100. Hereinafter, differences from the first embodiment will be mainly described.

Specifically, in the first embodiment, the acid flow path 150 is a flow path configured to guide an acid to the mouthpiece side while passing through the flavor source 210. On the other hand, in Modification Example 1, an acid flow path 150, as shown in FIG. 3, is a flow path configured to guide an acid to a mouthpiece side without passing through a flavor source 210. In addition, the atomizing unit 111 (atomizer 111R) does not exist at the upstream of the acid source 112. In other words, an aerosol flow path 140 is a flow path configured to guide the aerosol generated by the atomizing unit 111 (atomizer 111R) to the mouthpiece side without passing through the acid source 112.

Here, the acid flow path 150 is spatially partitioned from the aerosol flow path 140. Here, it is to be noted that the paraphrase "spatially partitioned" means that the aerosol flow path 140 and the acid flow path 150 are spatially separated from each other on the upstream side of a configuration provided to mix the flavor component captured by the aerosol and the acid with each other (in FIG. 3, mixing chamber 110C).

In more detail, the aerosol flow path 140 and the acid flow path 150 are partitioned from each other by a partitioning part 110D provided at the inhalator main body 100. The cartridge 200 described above is disposed in the aerosol flow path 140. Incidentally, it is to be noted that the partitioning part 110D partitions the aerosol flow path 140 and the acid flow path 150 from each other on the upstream side of the mixing chamber 110C.

In Modification Example 1, the flavor component captured by the aerosol generated from the atomizing unit 111 and the acid released from the acid source 112 are mixed with each other in the mixing chamber 110C provided at a downstream compared to the cartridge 200. That is, the mixing chamber 110C is provided at the downstream compared to the filter 230 provided to prevent slippage of the raw material piece constituting the flavor source 210. In addition, the flavor source 210 is provided between the acid source 112 and the atomizing unit 111, in the flow path communicating with the acid source 112 and the atomizing unit 111. In more detail, it is preferable that the flavor source 210 be provided between the acid source 112 and the atomizing unit 111, in all of the flow path communicating with the acid source 112 and the atomizing unit 111 at the downstream of the acid source 112.

That is, it is to be noted that, in the example shown in FIG. 3, after the cartridge 200 has been connected to the inhalator main body 100, even if an airflow from the downstream to the upstream arises, the acid generated from the acid source 112 is hardly directly guided to the atomizing unit 111.

Here, it is to be noted that the members constituting the acid flow path 150 (such as cylinder 100X and partitioning part 110D, for example) are composed of members having acid resistivity.

(Functions and Advantageous Effects)

In Modification Example 1, as in the first embodiment, the acid flow path 150 configured to guide an acid to the mouthpiece side without passing through the atomizing unit 111R is provided and thus the flavor can be improved while degradation of the members constituting the atomizing unit 111 is restrained.

In Modification Example 1, the acid flow path 150 is a flow path configured to guide an acid to the mouthpiece side without passing through the flavor source 210. Therefore, the acid generated from the acid source 112 is guided to the mouthpiece side without being filtrated by the flavor source 210 and thus the flavor can be improved while a loss of the acid is restrained. In particular, when water solution obtained by adding water of which weight ratio is 10 times to the flavor source 210 has alkaline pH, the acid generated from the acid source 112 is guided to the mouthpiece side without being neutralized by the flavor source 210 and thus the flavor can be improved while a loss of the acid is further restrained.

In Modification Example 1, the atomizing unit 111 (atomizer 111R) does not exist at the upstream of the acid source 112. In other words, the aerosol flow path 140 is a flow path configured to guide the aerosol generated by the atomizing unit 111 (atomizer 111R) without passing through the acid source 112. Therefore, the aerosol is not filtrated by the acid source 112, and the flavor can be improved while a loss of the aerosol is restrained.

Modification Example 2

Figure 4:
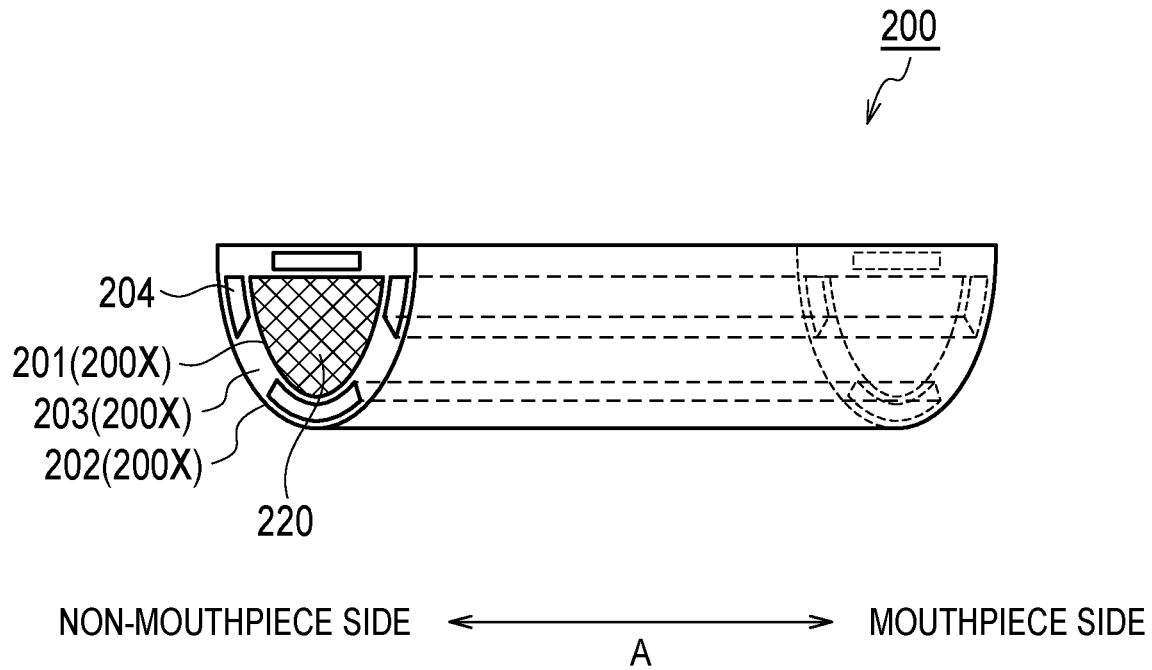
FIG. 4 is a view for illustrating a cartridge 200 according to Modification Example 2.
Figure 5:
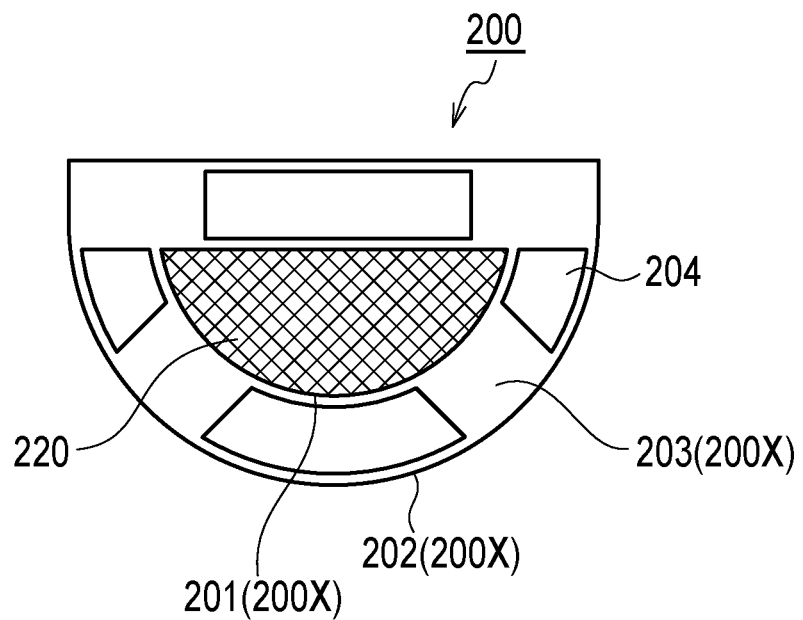
FIG. 5 is a view for illustrating the cartridge 200 according to Modification Example 2.
Figure 6:
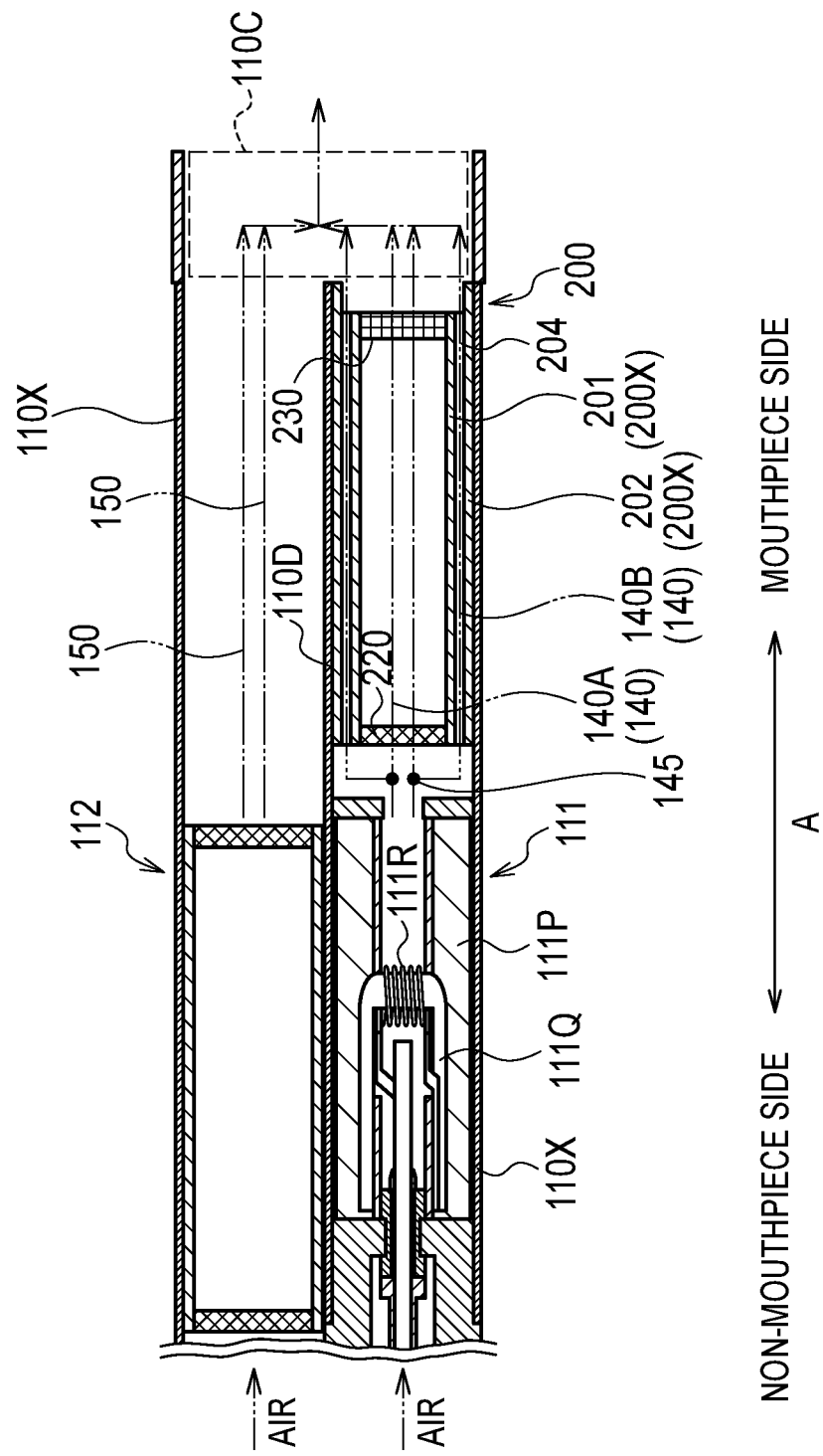
FIG. 6 is a view for illustrating an aerosol flow path 140 and an acid flow path 150 according to Modification Example 2.

Hereinafter, Modification Example 2 of the first embodiment will be described with reference to FIG. 4 to FIG. 6. FIG. 4 is a perspective view of a cartridge 200 according to Modification Example 2, and FIG. 5 is a view when the cartridge 200 according to Modification Example 2 is seen from a mouthpiece side. FIG. 6 is a sectional schematic view showing an internal structure of a flavor inhalator 10 in a state where the cartridge 200 has been connected to an inhalator main body 100. Hereinafter, differences from the first embodiment will be mainly described.

Specifically, in the first embodiment, the aerosol flow path 140 is composed of the first flow path configured to guide an aerosol to the mouthpiece side while passing through the flavor source 210. On the other hand, in Modification Example 2, an aerosol flow path 140, in addition to a first flow path configured to guide an aerosol to the mouthpiece side through a flavor source 210, includes a second flow path which is different from the first flow path. In addition, the atomizing unit 111 (atomizer 111R) does not exist at the upstream of the acid source 112. In other words, the aerosol flow path 140 is a flow path configured to guide the aerosol generated by the atomizing unit 111 (atomizer 111R) to the mouthpiece side without passing through the acid source 112.

Incidentally, an acid flow path 150 is spatially partitioned from the aerosol flow path 140. Here, it is to be noted that the paraphrase "spatially partitioned" means that the aerosol flow path 140 and the acid flow path 150 are spatially separated from each other on the upstream side of a configuration provided to mix the flavor component captured by the aerosol and the acid with each other (in FIG. 6, mixing chamber 110C). In Modification Example 2, it is to be noted that the aerosol flow path 140 and the acid flow path 150 are partitioned from each other by a partitioning part 110D, and the partitioning part 110D partitions the aerosol flow path 140 and the acid flow path 150 from each other on the upstream side of the mixing chamber 110C.

In Modification Example 2, it is preferable that a reduction rate of an aerosol in the second flow path be smaller than a reduction rate of an aerosol in the first flow path. Here, the "reduction rate" is a rate (that is, (inflow quantity−outflow quantity) of the "aerosol quantity lost in flow path (inflow quantity−outflow quantity)" relative to the "aerosol quantity flowing in flow path (inflow quantity)".

In more detail, as shown in FIG. 4 and FIG. 5, the cartridge 200 has an inner body 201, an outer body 202, and a rib 203 as the cartridge main body 200X described above. Incidentally, it is to be noted that, in FIG. 4, the flavor source 210 described above is omitted.

The inner body 201 has a cylindrical shape extending along the predetermined direction A. The inner body 201 houses the flavor source 210. On a non-mouthpiece side of the inner body 201, a mesh 220 is provided, and on a mouthpiece side of the inner body 201, a filter 230 is provided.

The outer body 202 has a cylindrical shape extending along the predetermined direction A. The outer body 202 houses the inner body 201. The outer body 202 is fixed to the inner body 201 by the rib 203 extending along the predetermined direction A. Between the ribs 203 adjacent to each other, a void 204 extending along the predetermined direction A is formed.

As shown in FIG. 6, in the case of using the cartridge 200 according to Modification Example 2, the aerosol flow path 140 includes: a first flow path 140A configured to guide an aerosol to the mouthpiece side while passing through the flavor source 210; and a second flow path 140B which is different from the first flow path 140A. A reduction rate of an aerosol in the second flow path 140B is smaller than a reduction rate of an aerosol in the first flow path 140A. Further, it is preferable that the amount of the aerosol guided to the mouthpiece side while passing through the second flow path 140B be more than the amount of the aerosol guided to the mouthpiece side while passing through the first flow path 140A.

Incidentally, the first flow path 140A is a flow path passing through the inside of the inner body 201, and the second flow path 140B is a flow path passing through the void 204. In Modification Example 2, the second flow path 140B is a flow path configured to guide an aerosol to the mouthpiece side while passing through the flavor source 210. In addition, the second flow path 140B is substantially hollowed.

In Modification Example 2, both of the first flow path 140A and the second flow path 140B are mainly formed inside of the cartridge main body 200X, and the branch portion 145 between the first flow path 140A and the second flow path 140B is provided outside of the cartridge main body 200X.

In Modification Example 2, the flavor component captured by the aerosol generated from the atomizing unit 111 and the acid released from the acid source 112 are mixed with each other in the mixing chamber 110C provided at the downstream compared to the cartridge 200. That is, the mixing chamber 110C is provided at the downstream compared to the filter 230 provided to prevent slippage of the raw material piece constituting the flavor source 210. In addition, the flavor source 210 is provided between the acid source 112 and the atomizing unit 111, in a flow path communicating with the acid source 112 and the atomizing unit 111. It is preferable that the flavor source 210 be provided between the acid source 112 and the atomizing unit 111, in the path communicating with the acid source 112 and the atomizing unit 111. As shown in FIG. 6, it is sufficient if the flavor source 210 is provided between the acid source 112 and the atomizing unit 111, in the main path communicating with the acid source 112 and the atomizing unit 111 at the downstream of the acid source 112 (acid source 112, mixing chamber 110C, inside of the inner body 201, atomizing unit 111).

That is, it is to be noted that, in the example shown in FIG. 6, after the cartridge 200 has been connected to the inhalator main body 100, even if an airflow from the downstream to the upstream arises, the acid generated from the acid source 112 is hardly directly guided to the atomizing unit 111.

(Functions and Advantageous Effects)

In Modification Example 2, as in the first embodiment, the acid flow path 150 configured to guide an acid to the mouthpiece without passing through the atomizer 111 is provided and thus the flavor can be improved while degradation of the members constituting the atomizing unit 111 is restrained.

In Modification Example 2, the second flow path 140B that is different from the first flow path 140A configured to guide an aerosol to the mouthpiece side while passing through the flavor source 210 is provided, and the reduction rate of the aerosol in the second flow path 140B is smaller than the reduction rate of the aerosol in the first flow path 140A. In this manner, the shortage of aerosol can be efficiently compensated for by the aerosol passing through the second flow path 140B while the desired amount of the flavor component is removed from the flavor source 210 by the aerosol passing through the first flow path 140A. Therefore, a loss of consumption quantity of the aerosol source and energy quantity required for atomization can be reduced.

In Modification Example 2, the second flow path 140B is a flow path configured to guide an aerosol to the mouthpiece side without passing through the flavor source 210. Therefore, in the second flow path 140B, the aerosol is not filtrated by the flavor source 210 and thus reduction of the aerosol in the second flow path 140B is restrained, and the shortage of the aerosol can be efficiently compensated for. In addition, an event that degradation of the flavor source 210 is promoted by the aerosol passing through the second flow path 140B is restrained, and a loss of the consumption quantity of the aerosol source can be reduced.

In Modification Example 2, the second flow path 140B is substantially hollowed. Therefore, reduction of the aerosol in the second flow path 140B is further restrained, and the shortage of the aerosol can be efficiently compensated for.

In Modification Example 2, the amount of the aerosol guided to the mouthpiece side while passing through the second flow path 140B is more than the amount of the aerosol guided to the mouthpiece side while passing through the first flow path 140A. Therefore, a sufficient aerosol can be guided to the mouthpiece side while degradation of the flavor source 210 is restrained.

In Modification Example 2, the atomizing unit 111 (atomizer 111R) does not exist at the upstream of the acid source 112. In other words, the aerosol flow path 140 is a flow path configured to guide the aerosol generated by the atomizing unit 111 (atomizer 111R) to the mouthpiece side without passing through the acid source 112. Therefore, the aerosol is not filtrated by the acid source 112, and the flavor can be improved while a loss of the aerosol is restrained.

In Modification Example 2, the flavor source 210 is composed of the raw material piece configured to impart the flavor component to the aerosol generated from the atomizing unit 111. In this manner, the specific surface area increases more significantly in comparison with the molded member obtained by molding the cigarette material in a sheet shape or in an engraved manner and thus the flavor component is easily released from the raw material piece constituting the flavor source 210. Therefore, when the desired amount of the flavor component is imparted to the aerosol by the flavor source 210, the volume of the raw material piece constituting the flavor source 210 can be restrained, and the size of the member configured to house the flavor source 210 (here, cartridge main body 200X) can be restrained.

Further, if the raw material piece of which specific surface area is larger than that of the molded member obtained by molding the cigarette material in a sheet shape or in an engraved shape is used, the flavor source 210 is easily degraded; and however, as described above, degradation of the flavor source 210 is restrained by providing the second flow path 140B that is different from the first flow path 140A configured to guide an aerosol to the mouthpiece side while passing through the flavor source 210. That is, by employment of the raw material piece of which specific surface area is large and the second flow path 140B, the volume of the raw material piece constituting the flavor source 210 is restrained while degradation of the flavor source 210 is restrained, and the size of the member configured to house the flavor 210 (here, cartridge main body 200X) can be restrained.

Modification Example 3

Figure 7:
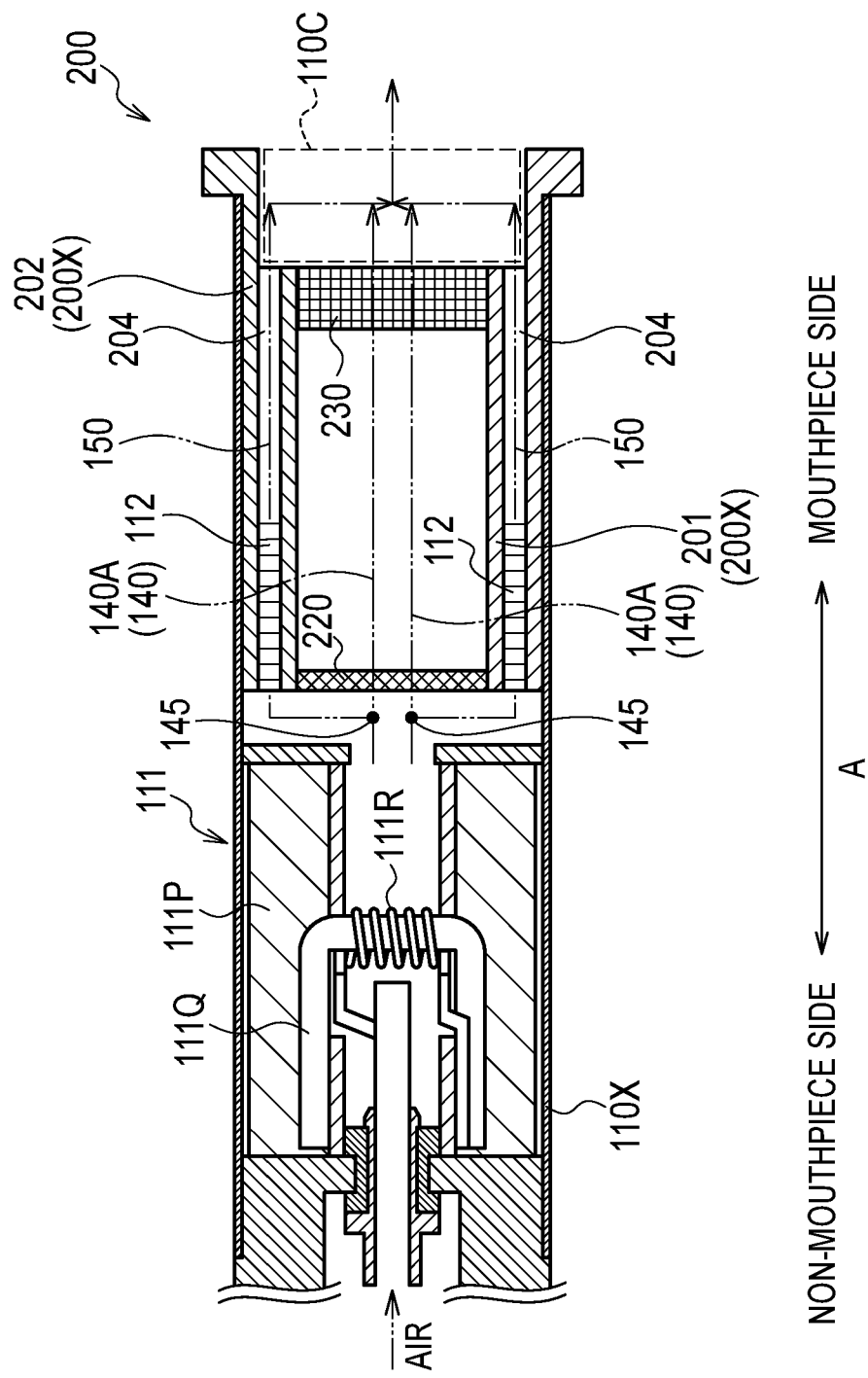
FIG. 7 is a view for illustrating an aerosol flow path 140 and an acid flow path 150 according to Modification Example 3.

Hereinafter, Modification Example 3 of the first embodiment will be described with reference to FIG. 7. FIG. 7 is a sectional schematic view showing an internal structure of a flavor inhalator 10 in a state where a cartridge 200 has been connected to an inhalator main body 100. Hereinafter, differences from Modification Example 2 will be mainly described.

Specifically, in Modification Example 2, the acid flow path 150 is provided separately from the second flow path 140B. On the other hand, in Modification Example 3, an acid flow path 150 is common to at least a part of a second flow path 10B. However, in Modification Example 3 as well, it is preferable that a reduction rate of an aerosol in a second flow path be smaller than a reduction rate of an aerosol in a first flow path. Although the reduction rate of the aerosol (that is, in a void in which an acid source is provided) is partially larger than that in the first flow path 140A, it is preferable that the reduction rate of the aerosol in the entire second flow path 140B be smaller than the reduction rate in the first flow path 140A.

In more detail, in Modification Example 3, an acid source 112, as shown in FIG. 7, is not disposed in line with an atomizing unit 1 in the vertical direction relative to the predetermined direction A, this source is provided at the downstream of the atomizing unit 111. In Modification Example 3, the acid source 112 is disposed in a void 204 of the cartridge 200 described above (that is, second flow path 140B).

When a plurality of voids 204 are provided in the cartridge 200, the acid source 112 may be disposed in all of the plurality of voids 204 or the acid source 112 may be disposed in a part of the plurality of voids 204.

That is, the entirety of the acid flow path 150 configured to guide the acid released from the acid source 112 is common to at least a part of the second flow path 140B composed of the voids 204. In other words, the voids 204 function as the acid flow path 150, and function as the second flow path 140B as well.

In Modification Example 3, in a state where the cartridge 200X has been connected to the inhalator main body 100, at least a part of the aerosol flow path 140 configured to guide the aerosol generated from the atomizing unit 111 configured to atomize the aerosol source without burning is formed, and at least a part of the acid flow path 150 configured to guide the acid generated from the acid source 112 to the mouthpiece side without passing through the atomizer 111R is formed. In Modification Example 3, at least a part of the aerosol flow path 140 and the entirety of the acid flow path 150 are formed of the cartridge main body 200X.

In Modification Example 3, the flavor captured by the aerosol generated from the atomizing unit 111 and the acid released from the acid source 112 are mixed with each other in a mixing chamber 110C provided at the downstream compared to the cartridge 200. That is, the mixing chamber 110C is provided at the downstream compared to a filter 230 provided to prevent slippage of the raw material piece constituting the flavor source 210.

(Functions and Advantageous Effects)

In Modification Example 3, as in the first embodiment, the acid flow path 150 configured to guide an acid to the mouthpiece side without passing through the atomizer 111R is provided and thus the flavor can be improved while degradation of the members constituting the atomizing unit 111 is restrained.

In Modification Example 3, there is no need to dispose the acid source 112 in line with the atomizing unit 111 in the vertical direction relative to the predetermined direction A. Therefore, when employing the configuration (refer to FIG. 3) forming the acid flow path 150 configured to guide an acid to the mouthpiece side without passing through the flavor source 210, there is no need for a dead space which is adjacent to the cartridge 200 in the vertical direction relative to the predetermined direction A. That is, by reducing the dead space inside of the flavor inhalator 10, it is possible to achieve downsizing of the flavor inhalator 10 in a vertical cross section relative to the predetermined direction A.

In Modification Example 3, the flavor source 210 and the acid source 112 are included in the cartridge 200 configured to be connectable to the inhalator main body 100 constituting the flavor inhalator 10. Therefore, attachment/detachment or replacement of the acid source 112 is easy. The entirety of the acid source 112 and the acid flow path 150 is accommodated in the cartridge 200, and the replacement frequency of the cartridge 200 is higher in comparison with the atomizing unit 111 and thus a condition for acid resistivity required for a member coming into contact with acid is mitigated. In addition, one cartridge 200 including an optimal (favorable) combination of the flavor source 210 and the acid in a set can be supplied.

Here, as in Modification Example 3, in an aspect of ventilating aerosol to the acid source 112, it is preferable that the acid included in the acid source 112 be dissolvable to the aerosol and be a nonvolatile or hardly volatile acid at normal temperature (for example, the acid having the steam pressure which is less than 0.1 kPa at 20° C.). In this manner, it is possible to supply a sufficient acid by using an aerosol as a carrier of the nonvolatile or hardly volatile acid while restraining migration of the acid to the flavor source 210 or the atomizer 111R.

Modification Example 4

Figure 8:
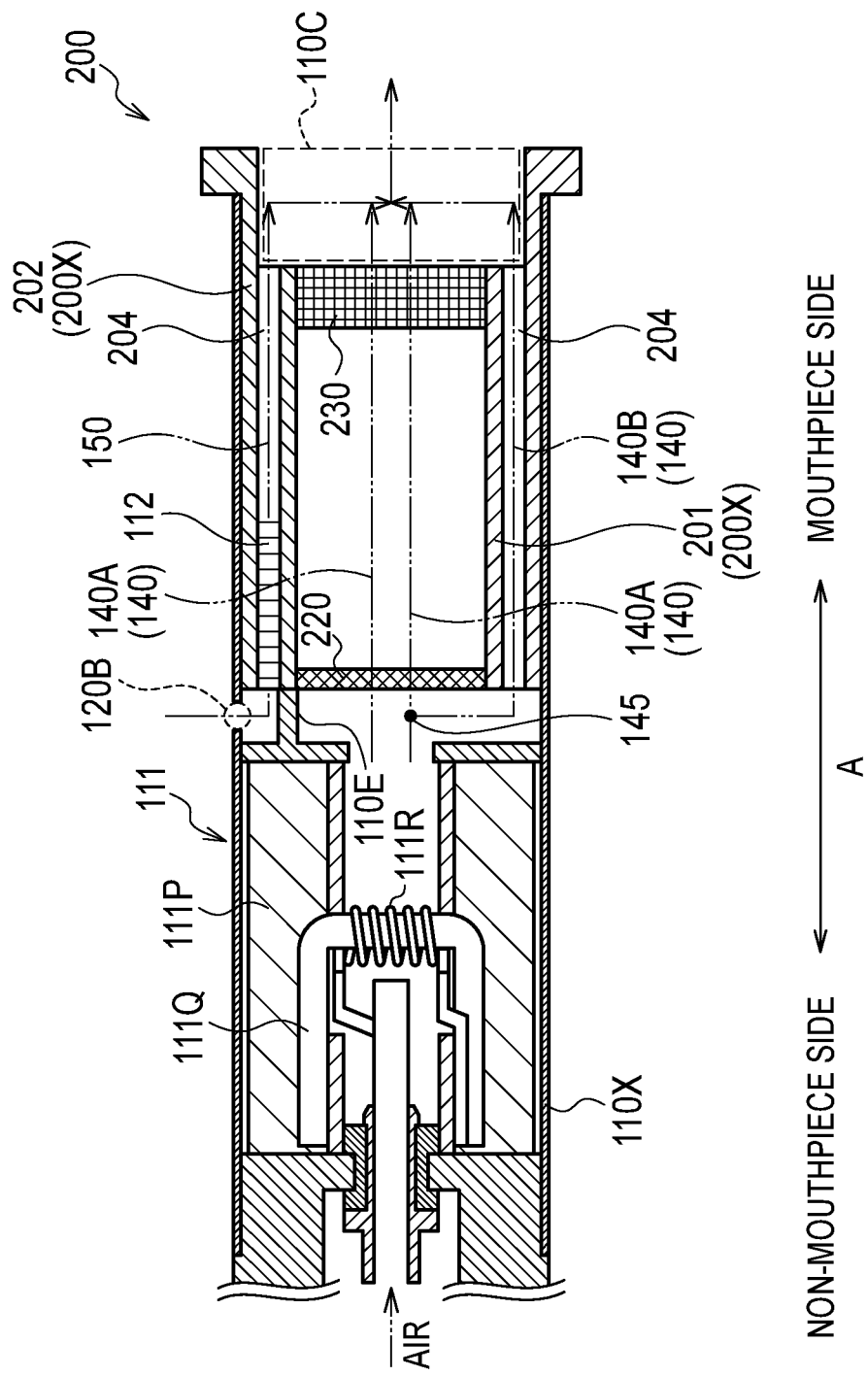
FIG. 8 is a view for illustrating an aerosol flow path 140 and an acid flow path 150 according to Modification Example 4.

Hereinafter, Modification Example 4 of the first embodiment will be described with reference to FIG. 8. FIG. 8 is a sectional schematic view showing an internal structure of a flavor inhalator 10 in a state where a cartridge 200 has been connected to an inhalator main body 100. Hereinafter, differences from Modification Example 3 will be mainly described.

Specifically, in Modification Example 3, in the flavor inhalator 10, the aerosol generated from the atomizing unit 111 is guided to the acid source 112. On the other hand, in Modification Example 4, a flavor inhalator 10, as shown in FIG. 8, has a ventilation hole 120B, and air introduced from the ventilation hole 120B is guided to an acid source 112. The ventilation hole 120B configured to guide air to the acid source 112 is provided separately from a ventilation hole 120A configured to guide air to the atomization to an atomizing unit 111. The ventilation hole 120B is provided on a mouthpiece side compared to the atomizing unit 111 in terms of a spatial layout which is not relevant to the upstream/downstream of an airflow path.

In Modification Example 4, the atomizing unit 111 (atomizer 111R) does not exist at the upstream of the acid source 112. In other words, the aerosol flow path 140 is a flow path configured to guide the aerosol generated by the atomizing unit 111 (atomizer 111R) to the mouthpiece side without passing through the acid source 112. An acid flow path 150 is spatially partitioned from the aerosol flow path 140. Here, it is to be noted that the paraphrase "spatially partitioned" means that the aerosol flow path 140 and the acid flow path 150 are spatially separated from each other on the upstream side of the configuration provided to mix the flavor component captured by the aerosol and the acid with each other (in FIG. 8, mixing chamber 110C).

Here, the flow path of the air introduced from the ventilation hole 120B is partitioned by a partitioning part 110E from the flow path of the aerosol generated from the atomizing unit 111 so that the air introduced from the ventilation hole 120B is not mixed with the aerosol generated from the atomizing unit 111. It is to be noted that the partitioning part 110E partitions the aerosol flow path 140 and the acid flow path 150 from each other on the upstream side of the mixing chamber 110C. It is to be noted that a void 204 which does not communicate with the ventilation hole 120B may form the second flow path 140B described above. Alternatively, the acid source 112 may be provided in the void 204 that does not communicate with the ventilation hole 120B as well.

In Modification Example 4, the flavor component captured by the aerosol generated from the atomizing unit 111 and the acid released from the acid source 112 are mixed with each other in the mixing chamber 110C provided at the downstream compared to the cartridge 200. That is, the mixing chamber 110C is provided at the downstream compared to a filter 230 provided to prevent slippage of the raw material piece constituting the flavor source 210. In addition, the flavor source 210 is provided between the acid source 112 and the atomizing unit 111, in a path communicating with the acid source 112 and the atomizing unit 111. In more detail, it is preferable that the flavor source 210 be provided between the acid source 112 and the atomizing unit 111 in the path communicating with the acid source 112 and the atomizing unit 111. As shown in FIG. 8, it is sufficient if the flavor source 210 is provided between the acid source 112 and the atomizing unit 111 in a main path communicating with the acid source 112 and the atomizing unit 111 at the downstream of the acid source 112 (acid source 112, mixing chamber 110C, inside of internal body 201, atomizing unit 111).

That is, it is to be noted that, in the example shown in FIG. 8, after the cartridge 200 has been connected to the inhalator main body 100, even if an airflow from the downstream to the upstream arises, the acid generated from the acid source 112 is hardly directly guided to the atomizing unit 111.

Incidentally, in Modification Example 4, the ventilation hole 120B needs to communicate with the void 204 when the cartridge 200 is connected to the inhalator main body 100 so that the air introduced from the ventilation hole 120B is guided to the void 204 (airflow path) in which the acid source 112 is provided. Therefore, it is preferable that at least one of the cartridge 200 and the inhalator main body 100 has a positioning function for specifying a relative position between the inhalator main body 100 and the cartridge 200 so that the ventilation hole 120B communicates with the void 204 (airflow path). An example of such a positioning function is as shown below.

Here, when the cartridge is rotatably mounted to the inhalator main body while a long axis direction (predetermined direction A) of the inhalator main body is defined as a rotating axis, it is preferable that one of the cartridge and the inhalator main body have a flow path provided in an annular manner about the rotating axis (annularly continuous flow path or a plurality of flow paths disposed in annular manner), and the other one of the cartridge and the inhalator main body have a flow path at a corresponding position in a radial direction relative to the flow path provided on one side. In this manner, in a circumferential direction about the long axis direction (predetermined direction A) of the inhalator main body, even if the cartridge is connected to the inhalator main body, the ventilation hole communicates with the flow path without considering the relative position between the inhalator main body and the cartridge.

Alternatively, in the circumferential direction about the predetermined direction A, in order to uniquely specify the relative position between the inhalator main body and the cartridge, it may be that a guide rib is provided on an interior face of a cylinder constituting the inhalator main body or a guide groove is provided on an exterior face of the cartridge main body. Conversely, it may be that a guide groove is provided on the interior face of the cylinder constituting the inhalator main body or a guide rib is provided on the exterior face of the cartridge main body. It is preferable that the guide groove and the guide rib have a shape extending along the predetermined direction A.

Alternatively, let us consider a case in which the cylinder constituting the inhalator main body has a polygonal or elliptical cavity and the cartridge has a polygonal columnar shape or an elliptical columnar shape. In such a case, it is preferable that the cylinder constituting the inhalator main body and the cartridge have a shape in which the relative position between the inhalator main body and the cartridge is uniquely specified. Alternatively, the inhalator main body and the cartridge may have a guide rib or a guide groove for uniquely specifying the relative position between the inhalator main body and the cartridge.

Alternatively, the inhalator main body and the cartridge may have a sign for uniquely specifying the relative position between the inhalator main body and the cartridge.

(Functions and Advantageous Effects)

In Modification Example 4, in addition to the advantageous effects of Modification Example 2 and Modification Example 3, advantageous effects shown below are attained. Specifically, the acid flow path 150 is a flow path configured to guide an acid to the mouthpiece side without passing through the flavor source 210. Therefore, the acid generated from the acid source 112 is guided to the mouthpiece side without being filtrated by the flavor source 210 and thus the flavor can be improved while a loss of the acid is restrained. In particular, when a water solution obtained by adding water of which weight ratio is 10 times to the flavor source 210 has alkaline pH, the acid generated from the acid source 112 is guided to the mouthpiece side without being neutralized by the flavor source 210 and thus the flavor can be improved while a loss of the acid is further restrained.

Modification Example 5

Figure 9:
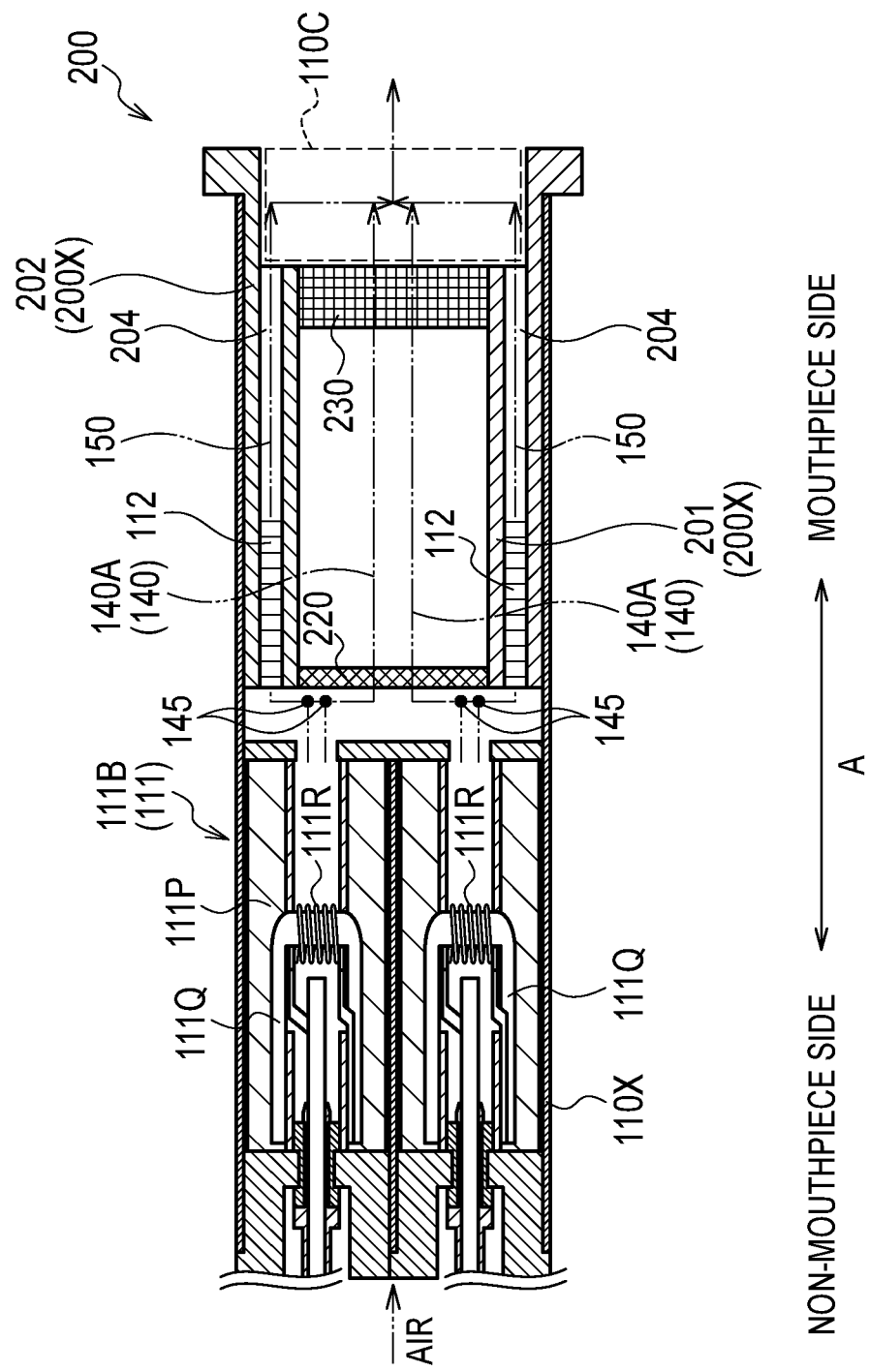
FIG. 9 is a view for illustrating an aerosol flow path 140 and an acid flow path 150 according to Modification Example 5.

Hereinafter, Modification Example 5 of the first embodiment will be described with reference to FIG. 9. FIG. 9 is a sectional schematic view showing an internal structure of a flavor inhalator 10 in a state where a cartridge 200 has been connected to an inhalator main body 100. Hereinafter, differences from Modification Example 3 will be mainly described.

Specifically, in Modification Example 3, the flavor inhalator 10 has a single unit as the atomizing unit 111 configured to atomize the aerosol source without burning. On the other hand, in Modification Example 5, the flavor inhalator 10, as shown in FIG. 9, has a first atomizing unit 111A and a second atomizing unit 111B as atomizing units 111 configured to atomize an aerosol source without burning. Here, the aerosols generated from the first atomizing unit 111A and the second atomizing unit 111B may be mixed with each other before being guided to the cartridge 200.

Incidentally, in FIG. 3, a layout of the first flow path 140A and the second flow path 140B is shown as an example, and a layout of the first atomizing unit 111A and the second atomizing unit 111B is shown as an example as well. Therefore, of course, the layout of the first atomizing unit 111A and the second atomizing unit 111B is not limited to an example shown in FIG. 9. In addition, the number of the first atomizing units 111A and the number of the second atomizing units 111B are arbitrary.

In Modification Example 5, an aerosol source atomized by the first atomizing unit 111A may be different from an aerosol source atomized by the second atomizing unit 111B. For example, it may be that the aerosol source atomized by the first atomizing unit 111A is composed of a substance configured to generate the aerosol that is capable of easily removing the flavor from the flavor source 210, and that the aerosol source atomized by the second atomizing unit 111B is composed of a substance configured to generate the aerosol including flavor. However, the aerosol source atomized by the first atomizing unit 111A may be the same as the aerosol source atomized by the second atomizing unit 111B.

Here, the acid source 112, as in Modification Example 3, is disposed in the void 204 of the cartridge 200 described above (that is, second flow path 140B).

When the plurality of voids 204 are provided in the cartridge 200, the acid source 112 may be disposed in all of the plurality of voids 204 or the acid source 112 may be disposed in a part of the plurality of the voids 204.

That is, the entirety of the acid flow path 150 configured to guide the acid released from the acid source 112 to the mouthpiece side is common to the second flow path 140B composed of the voids 204. In other words, the voids 204 function as the acid flow path 150 and function as the second flow path 140B as well.

Here, as in Modification Example 5, in an aspect of ventilating the aerosol to the acid source 112, it is preferable that the acid included in the acid source 112 be dissolvable to the aerosol and be a nonvolatile or hardly volatile acid at a normal temperature (for example, an acid having a steam pressure which is less than 0.1 kPa at 20° C.). In this manner, it is possible to supply a sufficient acid by using the aerosol as a carrier of the nonvolatile or hardly volatile acid while migration of the acid to the flavor source 210 or the atomizer 111R is restrained.

SUMMARY OF THE EMBODIMENT

Hereinafter, summary of the embodiment will be described. FIG. 10 to FIG. 22 are conceptual views for illustrating a positional relationship between the constituent members (such as acid source, atomizer, flavor source, and mixing chamber) provided in a non-burning type flavor inhaler and flow paths connecting the constituent members. As shown in FIG. 10 to FIG. 22, the non-burning type flavor inhaler comprises at least an acid source, an atomizer, and a flavor source, and has an acid flow path configured to guide the acid released from the acid source to the mouthpiece side without passing through the atomizer. Incidentally, in FIG. 10 to FIG. 22, the flavor source is, for example, a tobacco source (having alkaline pH in water solution obtained by adding water of which weight ratio is 10 times to the tobacco source).

Figure 10:
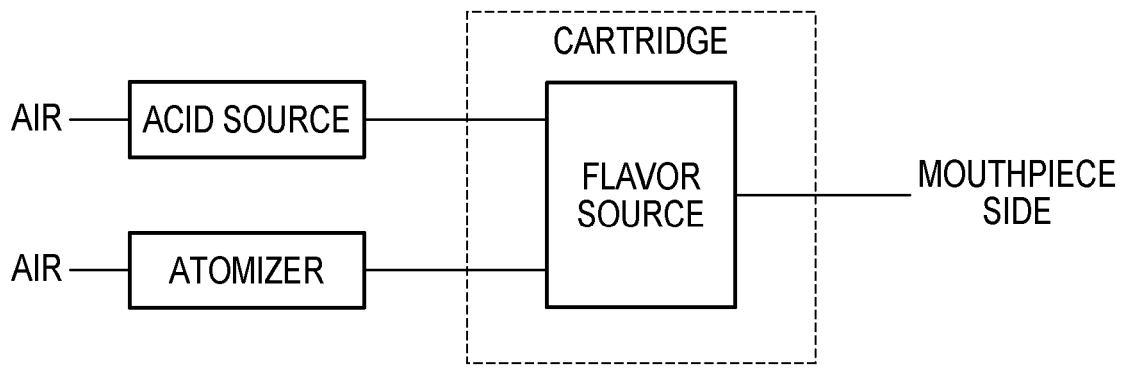
FIG. 10 is a conceptual view for illustrating the non-burning type flavor inhaler according to the embodiment.

First, a concept of the first embodiment (FIG. 2) will be described with reference to FIG. 10. As shown in FIG. 10, the acid released from an acid source and the aerosol generated from an atomizer are guided to a flavor source. The acid and the flavor component captured by the aerosol are mixed with each other in the flavor source. In other words, the flavor source is compatible with a mixing chamber configured to mix the acid and the flavor component with each other as well.

Figure 11:
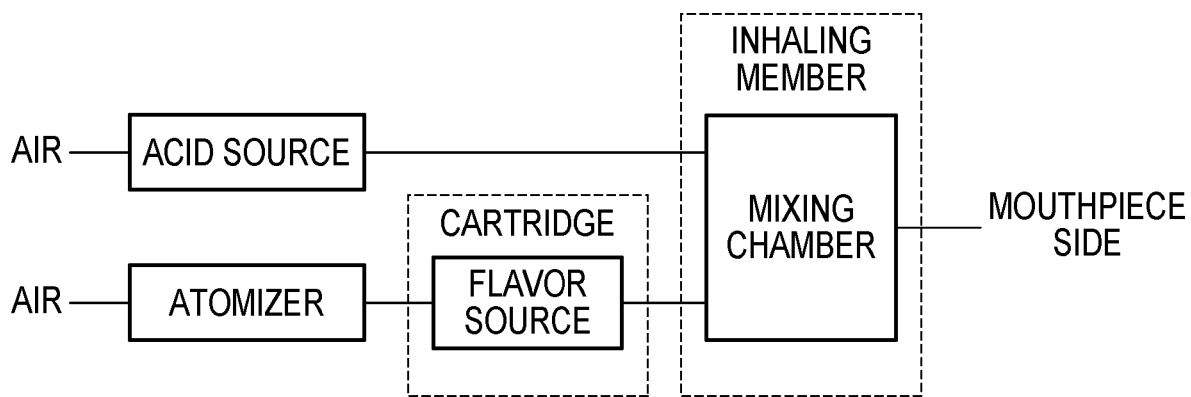
FIG. 11 is a conceptual view for illustrating the non-burning type flavor inhaler according to the embodiment.

Second, a concept of Modification Example 1 (FIG. 3) will be described with reference to FIG. 11. The acid released from an acid source is guided to a mixing chamber. The aerosol generated from an atomizer is guided to the mixing chamber through a flavor source. The mixing chamber is provided in an inhalation member, for example. The acid and the flavor captured by the aerosol are mixed with each other in the mixing chamber.

Figure 12:
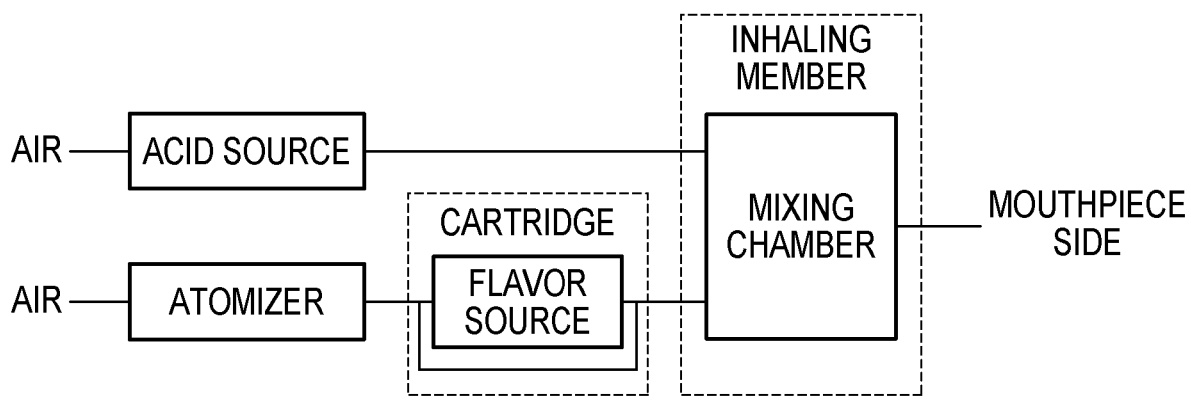
FIG. 12 is a conceptual view for illustrating the non-burning type flavor inhaler according to the embodiment.

Third, a concept of Modification Example 2 (FIG. 6) will be described with reference to FIG. 12. The acid released from an acid source is guided to a mixing chamber. The aerosol generated from an atomizer is guided to the mixing chamber through a flavor source and is guided to the mixing chamber without passing through the flavor source. The mixing chamber is provided in the inhalation member, for example. The cartridge having the flavor source (flavor source unit), in addition to a first flow path configured to guide the aerosol to the mouthpiece side while passing through the flavor source, has a second flow path configured to guide the aerosol to the mouthpiece side without passing through the flavor source. The acid and the flavor component captured by the aerosol are mixed with each other in the mixing chamber.

Figure 13:
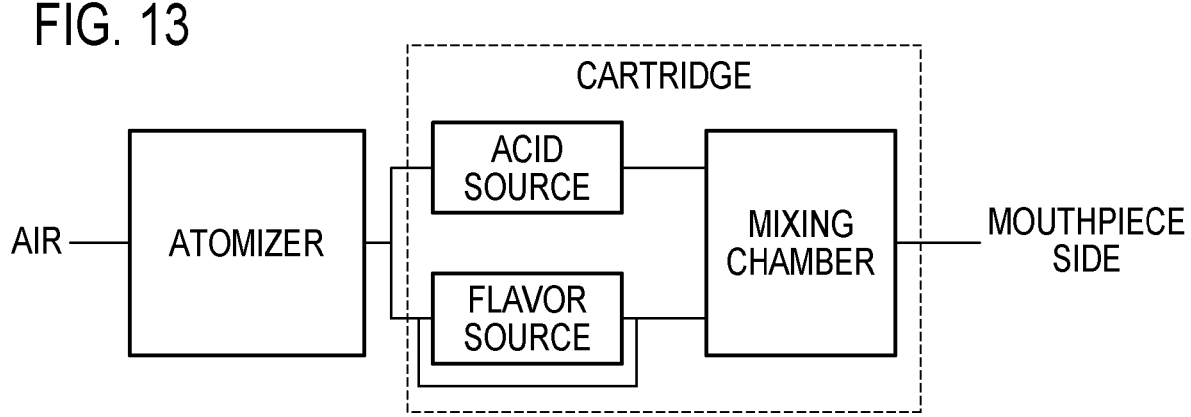
FIG. 13 is a conceptual view for illustrating the non-burning type flavor inhaler according to the embodiment.

Fourthly, a concept of Modification Example 3 (FIG. 7) will be described with reference to FIG. 13. The aerosol generated from an atomizer is guided to a mixing chamber through an acid source and is guided to the mixing chamber while passing through a flavor source. The acid source, the flavor source, and the mixing chamber constitute a cartridge (flavor unit). The cartridge, in addition to a first flow path configured to guide the aerosol to a mouthpiece side while passing through the flavor source, may have a second flow path configured to guide the aerosol to the mouthpiece side without passing through the flavor source. The acid and the flavor captured by the aerosol are mixed with each other in the mixing chamber.

Figure 14:
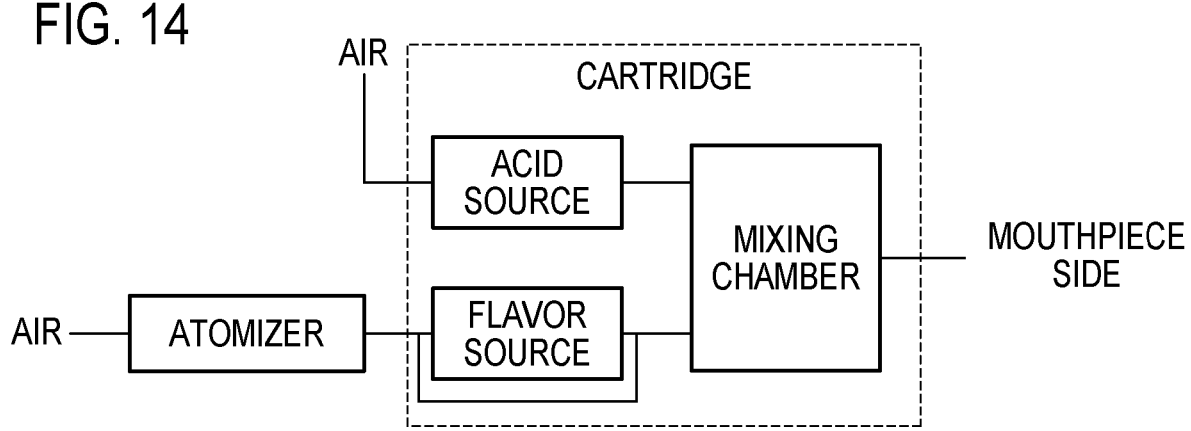
FIG. 14 is a conceptual view for illustrating the non-burning type flavor inhaler according to the embodiment.

Fifthly, a concept of Modification Example 4 (FIG. 8) will be described with reference to FIG. 14. The aerosol generated from an atomizer is guided to a mixing chamber through a flavor source. The acid released from an acid source is guided to the mixing chamber. The acid source, the flavor source, and the mixing chamber constitute a cartridge (flavor source unit). Here, a ventilation hole for introducing air to the acid source is different from a ventilation hole for introducing air to the atomizer. The cartridge, in addition to a first flow path configured to guide the aerosol to a mouthpiece side while passing through the flavor source, may have a second flow path configured to guide the aerosol to the mouthpiece side without passing through the flavor source. The acid and the flavor component captured by the aerosol are mixed with each other in the mixing chamber.

As shown above, although each concept of the embodiment has been described, the positional relationship between the constituent members provided in the non-burning type flavor inhaler and the flow paths connecting the constituent members is not limited thereto. For example, the embodiment may include aspects shown below.

Figure 15:
FIG. 15 is a conceptual view for illustrating the non-burning type flavor inhaler according to the embodiment.
Figure 16:
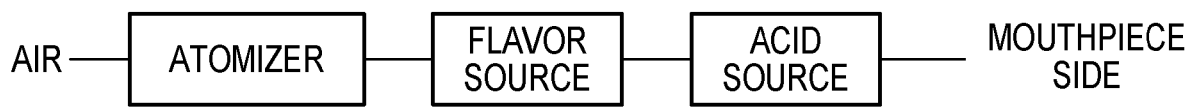
FIG. 16 is a conceptual view for illustrating the non-burning type flavor inhaler according to the embodiment.

For example, as shown in FIG. 15 and FIG. 16, the atomizer, the acid source, and the flavor source may be arranged in series from the upstream towards the downstream. For example, these constituent elements, as shown in FIG. 15, may be arranged in series in sequential order of the atomizer, the acid source, and the flavor source from the upstream towards the downstream. Incidentally, in the example shown in FIG. 15, the acid and the flavor component captured by the aerosol are mixed with each other in the flavor source. In other words, the flavor source is compatible with a mixing chamber configured to mix the acid and the flavor component with each other. Alternatively, as shown in FIG. 16, the atomizer, the flavor source, and the acid source may be arranged in series in sequential order from the upstream towards the downstream. Incidentally, in the example shown in FIG. 16, the acid and the flavor component captured by the aerosol are mixed with each other in the acid source. In other words, the aid source is compatible with the mixing chamber configured to mix the acid and the flavor component with each other.

Figure 17:
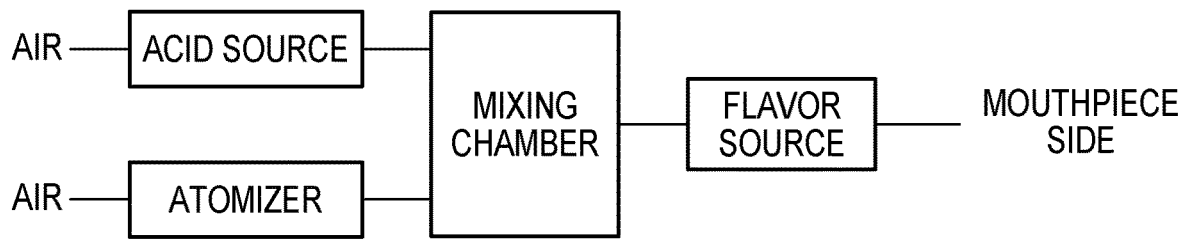
FIG. 17 is a conceptual view for illustrating the non-burning type flavor inhaler according to the embodiment.

Alternatively, as shown in FIG. 17, the aerosol generated from the atomizer and the acid released from the acid source may be guided to the flavor source after mixed in the mixing chamber.

Thus, it is to be noted that various modifications can occur with a configuration in which the acid released from the acid source is guided to the mouthpiece side without passing through the atomizer.

Further, a case in which the non-burning type flavor inhaler has a plurality of atomizers (first atomizer and second atomizer), as in Modification Example 5 (FIG. 9), will be described with reference to FIG. 18 to FIG. 22.

Figure 18:
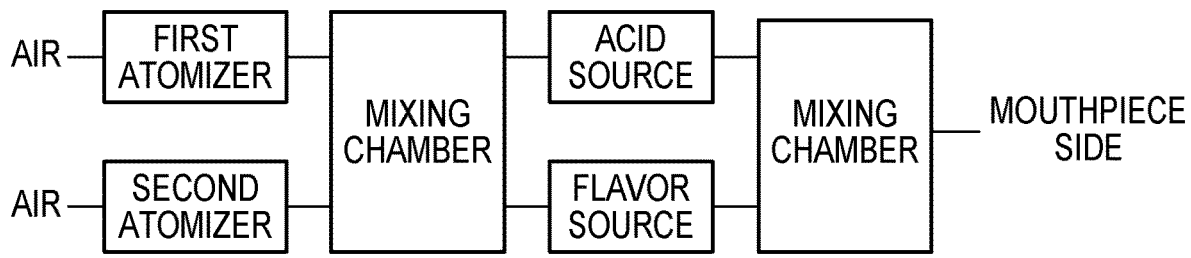
FIG. 18 is a conceptual view for illustrating the non-burning type flavor inhaler according to the embodiment.

For example, as shown in FIG. 18, the aerosols generated from a plurality of atomizers are respectively guided to an acid source and a flavor source after mixed with each other in a mixing chamber. The aerosol including the acid released from the acid source and the aerosol including the flavor trapped in the flavor source are mixed with each other in the mixing chamber. In such a case, the flow path passing through the acid source is the second flow path that does not pass through the flavor source. In such a case, it is preferable that the reduction rate of the aerosol in the second flow path be smaller than the reduction rate of the aerosol in the first flow path passing through the flavor source.

Figure 19:
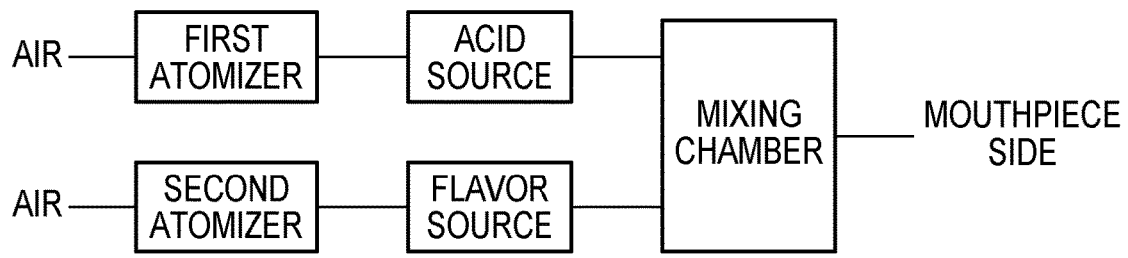
FIG. 19 is a conceptual view for illustrating the non-burning type flavor inhaler according to the embodiment.

Alternatively, as shown in FIG. 19, the aerosol generated from the first atomizer is guided to the acid source without being mixed with the aerosol generated from the second atomizer. The aerosol generated from the second atomizer is guided to the flavor source without being mixed with the aerosol generated from the first atomizer. The flow path of the aerosol generated from the first atomizer is the second flow path that does not pass through the flavor source, and the flow path of the aerosol generated from the second atomizer is the first flow path passing through the flavor source. In such a case, it is preferable that the reduction rate of the aerosol in the second flow path be smaller than the reduction rate of the aerosol in the first flow path.

Figure 20:
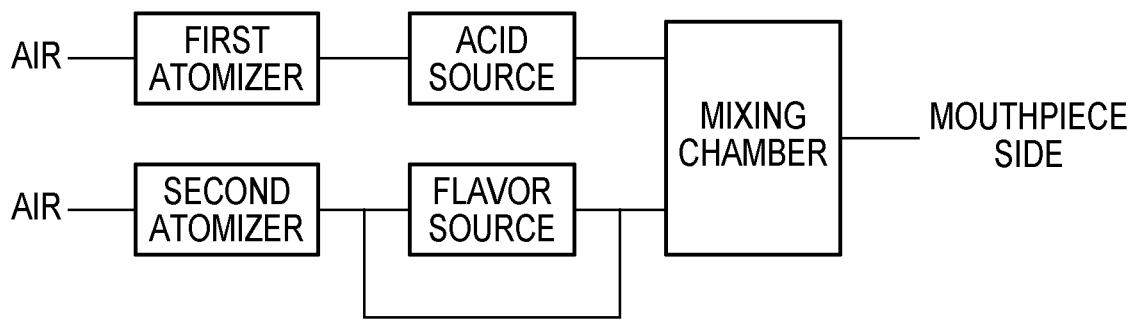
FIG. 20 is a conceptual view for illustrating the non-burning type flavor inhaler according to the embodiment.

Alternatively, as shown in FIG. 20, the aerosol generated from the first atomizer is guided to the acid source without being mixed with the aerosol generated from the second atomizer. The aerosol generated from the second atomization art is guided to the flavor source without being mixed with the aerosol generated from the first atomizer. The flow paths of the aerosol generated from the second atomizer include: a first flow path passing through the flavor source; and a second flow path A which does not pass through the flavor source. Incidentally, the flow path of the aerosol generated from the first atomizer is a second flow path B which does not pass through the flavor source as well. In such a case, it is preferable that the reduction rate of the aerosol in the second flow path A be smaller than the reduction rate of the aerosol in the first flow path. The reduction rate of the aerosol in the second flow path B may be smaller than the reduction rate of the aerosol in the first flow path.

Figure 21:
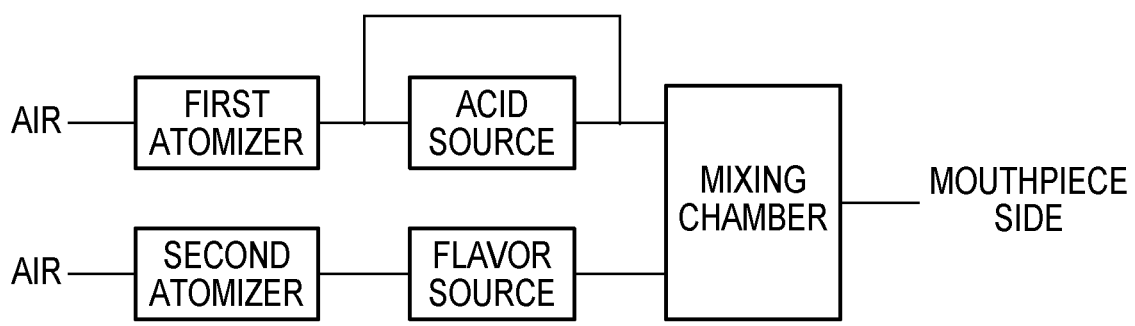
FIG. 21 is a conceptual view for illustrating the non-burning type flavor inhaler according to the embodiment.

Alternatively, as shown in FIG. 21, the aerosol generated from the first atomizer is guided to the acid source without being mixed with the aerosol generated from the second atomizer. The aerosol generated from the second atomizer is guided to the flavor source without being mixed with the aerosol generated from the first atomizer. The flow paths of the aerosol generated from the first atomizer include: a flow path passing through the acid source (hereinafter, referred to as "flow path A"); and a flow path which does not pass through the acid source (hereinafter, referred to as "flow path B"). In such a case, it is preferable that the reduction rate of the aerosol in the flow path B be smaller than the reduction rate of the aerosol in the flow path A.

Figure 22:
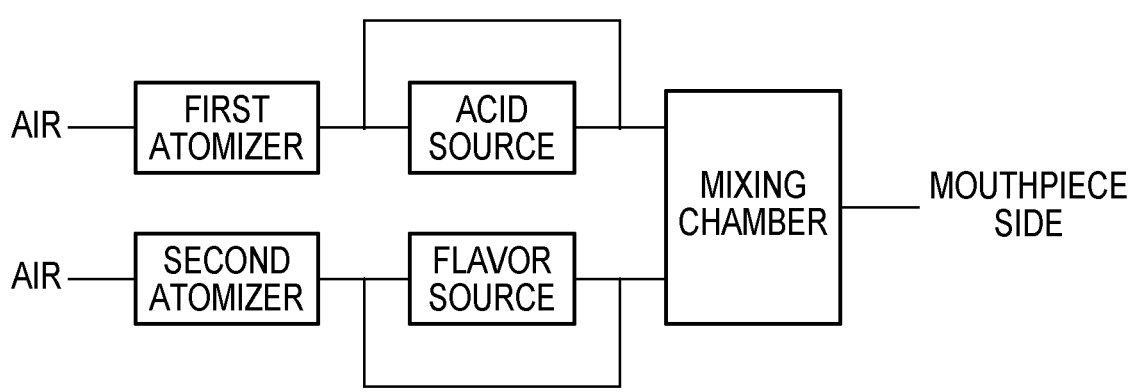
FIG. 22 is a conceptual view for illustrating the non-burning type flavor inhaler according to the embodiment.

Alternatively, as shown in FIG. 22, the embodiment may be a combination of FIG. 20 and FIG. 21. Specifically, it may be that the flow paths of the aerosol generated from the first atomizer include: a flow path passing through the acid source; and a flow path which does not pass through the acid source, and the flow paths of the aerosol generated from the second atomizer include: a flow path passing through the flavor source; and a flow path which does not pass through the flavor source.

Incidentally, in FIG. 18 to FIG. 22, the acid source and the flavor source may constitute a flavor unit. In such a case, the flow path of the aerosol generated from the first atomizer is an example of the second flow path, and the flow path of the aerosol generated from the second atomizer is an example of the first flow path.

Here, in the aspects of ventilating the aerosol for the acid source (FIG. 13, FIG. 15, FIG. 16, and FIG. 18 to FIG. 22), it is preferable that the acid included in the acid source be dissolvable to the aerosol and be a nonvolatile or hardly volatile acid at a normal temperature (for example, an acid having a steam pressure which is less than 0.1 kPa at 20° C.). In this manner, it is possible to supply a sufficient acid by using the aerosol as a carrier of the nonvolatile or hardly volatile acid while restraining migration of the acid to the flavor source or the atomizer.

Other Embodiments

Although the present invention has been described by way of the foregoing embodiment, it is not to be understood that the statements and drawings forming a part of this disclosure limits the present invention. From this disclosure, various substitute embodiments, examples, and operation techniques would be self-evident to one skilled in the art.

Although in the embodiment, the cartridge 200 does not include the atomizing unit 111, the embodiment is not limited thereto. For example, the cartridge 200 may constitute one unit together with the atomizing unit 111.

In the embodiment, the flavor source 210 is included in the cartridge 200 configured to be connectable to the inhalator main body 100 constituting the flavor inhalator 10. However, the embodiment is not limited thereto. For example, the inhalator main body 100 may house the flavor source 210 in place of using the cartridge 200.

The embodiment was described as to each of the cases in which a part of the second flow path 140B is formed of the voids 204 of the cartridge 200 (Modification Example 2 to Modification Example 5). However, the embodiment is not limited thereto. Specifically, a part of the second flow path 140B may be composed of a groove extending along the predetermined direction A in the exterior side face of the cartridge main body 200X of the cartridge 200. In addition, it is preferable that the reduction rate of the aerosol in the second flow path 10B be smaller than the reduction rate of the aerosol in the first flow path 10A. The number of times in the second flow path 1490B accessing the cartridge 200 towards the downstream of the aerosol flow path is not limited.

In the embodiment, a branch portion 145 between the first flow path 140A and the second flow path 140B is provided outside of the cartridge main body 200X. However, the embodiment is not limited thereto. The branch portion 145 may be provided inside of the cartridge main body 200X.

Although not set forth in particular in the embodiment, the atomizing unit 111 may be configured to be attachable/detachable or replaceable relative to the inhalator main body 100. Similarly, the acid source 112 may be configured to be attachable/detachable or replaceable relative to the inhalator main body 100. The atomizing unit 111 and the acid source 112 are configured by one unit, and may be configured to be attachable/detachable or replaceable relative to the inhalator main body 100. That is, the atomizing unit 111, the acid source 112, and the flavor source 210 may be respectively separately provided as a replaceable unit relative to an electric unit (second unit 120). Alternatively, among the atomizing unit 111, the acid source 112, and the flavor source 210, a unit including at least two or more constituent elements may be provided as a replaceable unit relative to the electric unit (second unit 120).

Although not set forth in particular in the embodiment, the first unit 110 having the atomizer 111R and the acid source 112 may constitute an atomizing unit configured to be attachable/detachable or replaceable relative to the electric unit (second unit 120). In such a case, the first unit 110 has a connector configured to connect the flavor source 210 (cartridge 200) at the downstream of the atomizer 111R so that the aerosol generated from the atomizer 111R is guided to the flavor source 210 (cartridge 200). The connector is a first cylinder 110X configured to house the atomizer 111R and the acid source 112, to which the cartridge 200 is to be connected.

Modification Example 5 exemplified a case in which the first atomizing unit 111A and the second atomizing unit 111B are provided in the non-burning type flavor inhaler 10. However, Modification Example 5 is not limited thereto. Specifically, a flavor source configured to generate a flavor such as menthol may be provided in place of the second atomizing unit 111B. Alternatively, in a state where the second atomizing unit 111B is provided in the same manner as that in Modification Example 1, the flavor source configured to generate the flavor such as menthol may be provided in the second flow path 140B.

In Modification Example 3 and Modification Example 5, among a plurality of voids 204 provided in the cartridge 200, nothing is provided in a void 204 in which the acid source 112 is not provided. However, Modification Example 3 and Modification Example 5 are not limited thereto. Specifically, in the void 204 in which the acid source 112 is not provided, a flavor source configured to generate a flavor such as menthol may be provided in the second flow path 140B. Alternatively, in a void 204 in which the acid source 112 is provided, the flavor source configured to the flavor such as menthol may be provided.

It is preferable that a kind of the flavor source configured to generate the flavor such as menthol described above be different from a kind of the flavor source 210 included in the cartridge 200. For example, it is preferable that the flavor source configured to generate the flavor such as menthol be composed of a non-cigarette material.

INDUSTRIAL APPLICABILITY

According to the present invention, there can be provided a non-burning type flavor inhaler and a flavor source unit which are capable of improving a flavor while restraining degradation of a member constituting an atomizing unit.

The invention claimed is:

1. A non-burning type flavor inhaler comprising:
an atomizing unit having an atomizer configured to atomize an aerosol source without burning,
a flavor source provided on a mouthpiece side compared to the atomizing unit,
an acid source configured to release an acid,
an aerosol flow path configured to guide an aerosol generated from the atomizing unit to the mouthpiece side, and
an acid flow path configured to guide the acid released from the acid source to the mouthpiece side without passing through the atomizer, wherein
the aerosol flow path includes at least a first flow path configured to guide the aerosol to the mouthpiece side while passing through the flavor source,
the acid flow path and the first flow path have a common flow path, and
the flavor source is replaceable separately from the acid source relative to the non-burning type flavor inhaler.

2. The non-burning type flavor inhaler according to claim 1, wherein
the acid flow path is a flow path configured to guide an acid to the mouthpiece side without passing through the flavor source.

3. The non-burning type flavor inhaler according to claim 1, wherein
the flavor source is provided between the acid source and the atomizing unit, in a flow path communicating with the acid source and the atomizing unit at a downstream of the acid source.

4. The non-burning type flavor inhaler according to claim 3, wherein
the flavor source is provided between the acid source and the atomizing unit, in all of the flow path communicating the acid source and the atomizing unit at the downstream of the acid source.

5. The non-burning type flavor inhaler according to claim 1, wherein the flavor source is a tobacco source.

6. The non-burning type flavor inhaler according to claim 5, wherein
the flavor source is a tobacco source, and
the tobacco source has alkaline pH in water solution obtained by adding water of which weight ratio is 10 times to the tobacco source.

7. The non-burning type flavor inhaler according to claim 1, wherein
the acid flow path is a flow path configured to guide an acid to the mouthpiece side while passing through the flavor source.

8. The non-burning type flavor inhaler according to claim 1, wherein the aerosol flow path, in addition to the first flow path, includes a second flow path which is different from the first flow path.

9. The non-burning type flavor inhaler according to claim 8, wherein
a reduction rate of an aerosol in the second flow path is smaller than a reduction rate of an aerosol in the first flow path.

10. The non-burning type flavor inhaler according to claim 8, wherein the acid flow path is common to at least a part of the second flow path.

11. The non-burning type flavor inhaler according to claim 10, wherein
the acid source is provided in the second flow path.

12. The non-burning type flavor inhaler according to claim 8, wherein at least a part of the first flow path is a flow path of the aerosol generated from the atomizer, and
at least a part of the second flow path is a flow path of the aerosol generated from another atomizer which is different from the atomizer.

13. The non-burning type flavor inhaler according to claim 1, wherein the atomizer does not exist at an upstream of the acid source.

14. The non-burning type flavor inhaler according to claim 1, comprising:
a first ventilation hole for introducing air to the atomizing unit; and
a second ventilation hole provided separately from the first ventilation hole and configured to introduce an air to the acid source.

15. The non-burning type flavor inhaler according to claim 14, comprising:
a flavor source unit having the flavor source and a unit main body configured to house the flavor source, wherein
the unit main body is configured to connectable to an inhalator main body constituting the non-burning type flavor inhaler,
the inhalator main body has the second ventilation hole,
the unit main body has an airflow path in which the acid source is provided, and
at least one of the inhalator main unit and the unit main body has a positioning function for specifying a relative position between the inhalator main body and the unit main body so that the second ventilation hole communicates with the airflow path.

16. The non-burning type flavor inhaler according to claim 1, comprising:
a mixing chamber for mixing a flavor component captured by the aerosol generated from the atomizing unit and the acid released from the acid source.

* * * * *